(12) United States Patent
Haslam

(10) Patent No.: US 6,583,334 B1
(45) Date of Patent: Jun. 24, 2003

(54) OVARIECTOMIZED MOUSE MODEL FOR HUMAN MENOPAUSE

(75) Inventor: Sandra Z. Haslam, Laingsburg, MI (US)

(73) Assignee: Board of Trustees operating Michigan State University, East Lansing, MI (US)

(*) Notice: Subject to any disclaimer, the term of this patent is extended or adjusted under 35 U.S.C. 154(b) by 0 days.

(21) Appl. No.: 09/576,838

(22) Filed: May 23, 2000

(51) Int. Cl.[7] .................. A01K 67/00; A61K 39/00; A61K 51/00; G01K 33/00
(52) U.S. Cl. ................ 800/9; 800/3; 800/8; 424/9.2; 424/198.1
(58) Field of Search ................ 800/3, 8, 9; 424/198.1, 424/9.2

(56) References Cited

PUBLICATIONS

Raafat et al., A Mouse Model to Study the Effects of Hormone Replacement Therapy on Norma Mammary Gland during Menopause . . . , 1999, vol. 140, No. 6, pp. 2570–2580.*

Haslam et al., Long–term ovariectomy menopause and altered mammary gland hormonal responsiveness, 1992, Keystone Sysposium, p. 94.*

King et al., The Influence of Estrogen on Cancer Incidence and Adrenal Changes in Ovariectomized Mice on Calorie Restriction, 1949, Cancer Research, vol. 9, pp. 436–437.*

Jungblut et al., A Proposal for Assessment of Hormone Sensitivity and Consequent Endocrine Therapy of Breast Cancer, 1977, Europ. J. Cancer, vol. 13, pp. 1201–1202.*

Nelson et al., Altered Profiles of Estradiol and Progesterone Associated with Porlonged Estrous Cycles and Persistent Vaginal Cornification in Aging C57BL/6J Mice1, 1981, Bibology of Reproduction, vol. 24, pp. 784–794.*

EA Thorndike et al., Frontiers in Bioscience, "In Search of an Animal Model for Postmenopausal Diseases," Apr. 1998, 3, pp. 17–26.*

The Platypus, website, www.healthsci.utas.edu.au/physiol/mono/Platpage.html, pp. 1–3.*

* cited by examiner

Primary Examiner—Jeffrey Fredman
Assistant Examiner—Jon Eric Angell
(74) Attorney, Agent, or Firm—Ian C. McLeod

(57) ABSTRACT

A method for determining a response to a biologically active agent in ovariectomized lower test mammals is described. The mammals are divided into those which have an early time post ovariectomy and those which have a late time post ovariectomy and then each group is tested simultaneously with the agent. The method is used to simulate menopause in humans for the purpose of determining a positive or negative response and a possible treatment.

23 Claims, 18 Drawing Sheets

FIGURE 2A
FIGURE 2B
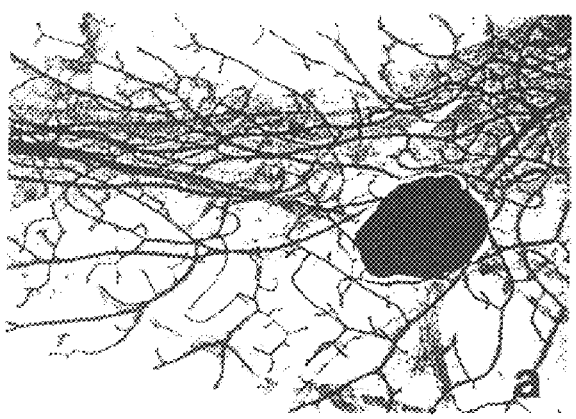
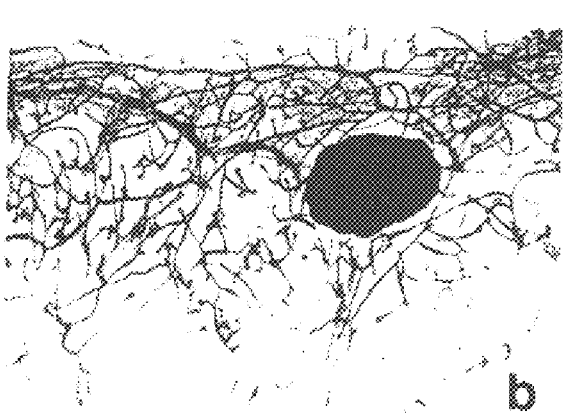
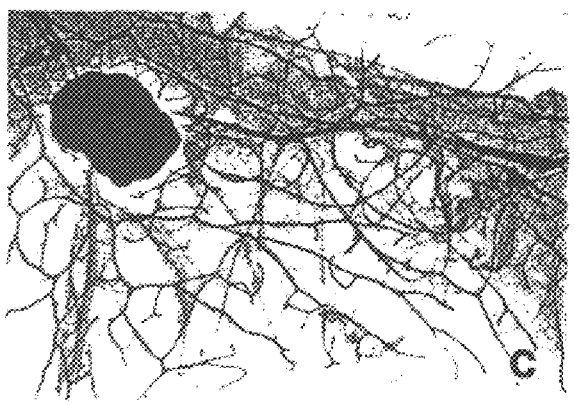
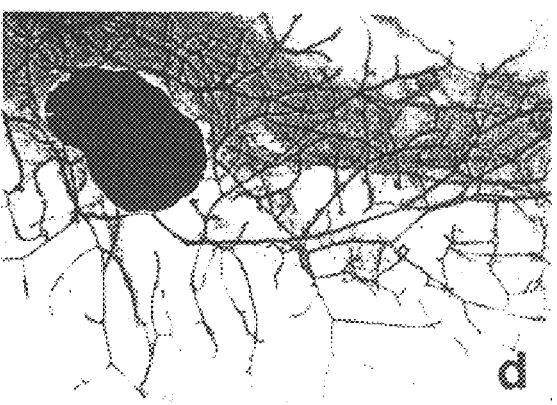
FIGURE 2C
FIGURE 2D

FIGURE 3A
FIGURE 3B
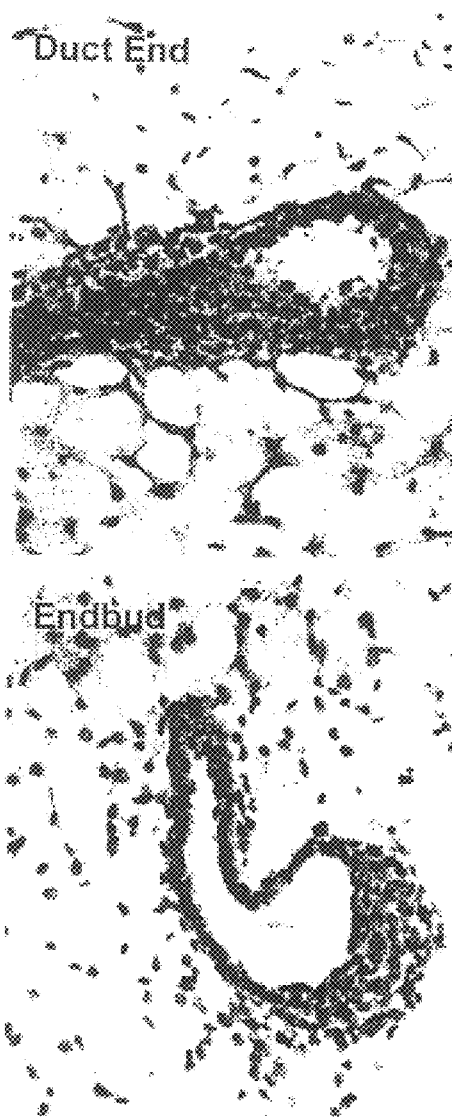
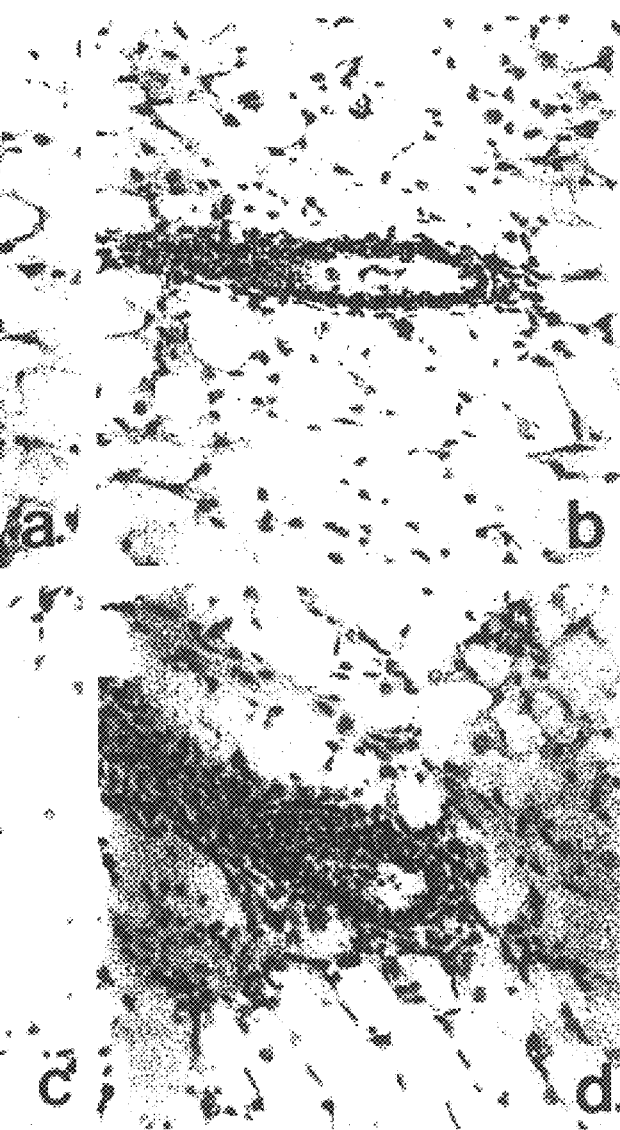
FIGURE 3C
FIGURE 3D

FIGURE 7A
FIGURE 7B
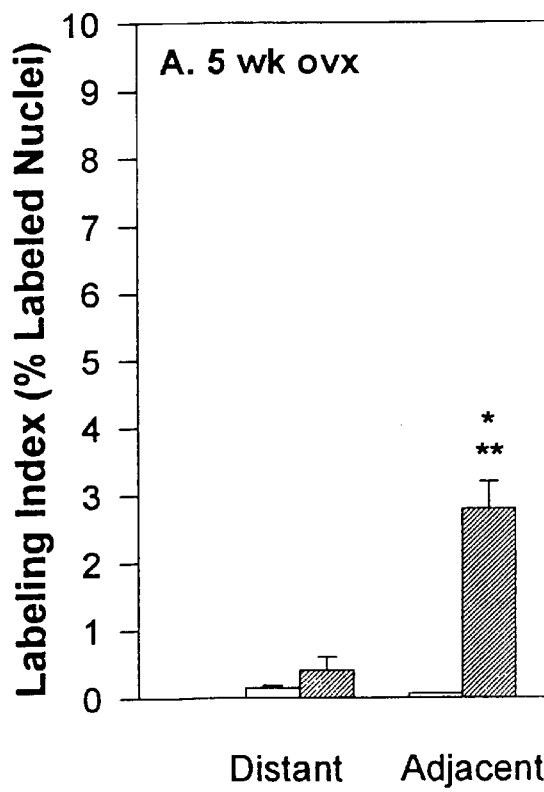
Stromal Cell Location in
Relation to Duct Ends

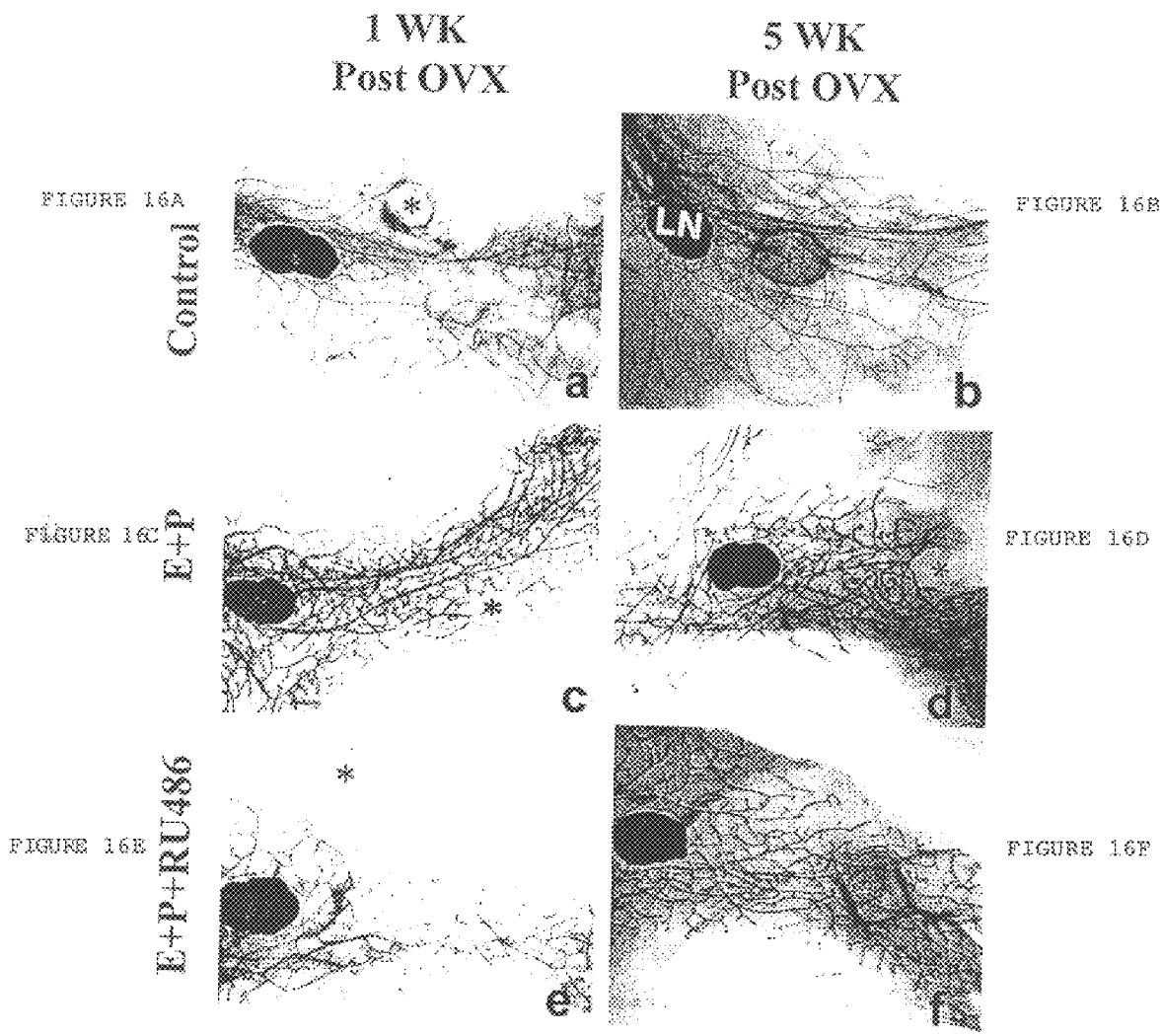

OVARIECTOMIZED MOUSE MODEL FOR HUMAN MENOPAUSE

STATEMENT REGARDING FEDERALLY SPONSORED RESEARCH OR DEVELOPMENT

This invention was sponsored under National Institutes of Health Contract No. 1RO1AG13059. The government has certain rights in this invention.

BACKGROUND OF THE INVENTION (1) Field of the Invention

The present invention relates to an mouse model for human menopause which provides a simulated comparison between early and late menopause. In particular the present invention uses time after an ovariectomy of the mouse to simulate early and late human menopause.

(2) Description of Related Art

Hormone replacement therapy (HRT) with estrogen in postmenopausal women is used to alleviate menopausal symptoms such as vasomotor and urogenital dysfunction, as well as to reduce the risk of bone fractures and cardiovascular disease, and it may also decrease the debilitating symptoms of Alzheimer's disease (Stampfer, M. J., et al., N Engl J Med 325:756–762 (1991); Riggs, B. L., et al., N Engl J Med 327:620–627 (1992); Compston, J. E., Br Med Bull 48:309–344 (1992); Col, F. N., et al., JAMA 277:1140–1147 (1997); The writing group of PEPI trial, JAMA 276:1389–1396 (1996); Henderson, V. W., et al., Arch Neurol 51:896–900 (1994); and Ming-Xin, T., et al., The Lancet 348:429–432 (1996)). While most breast cancers occur in postmenopausal women, the role of menopause per se in the etiology of breast cancer is not known. However, there is solid epidemiological evidence for an important role of ovarian hormones in mammary cancer development (MacMahon, B., et al., J. Natl Cancer Inst 50:21–42 (1973)). Lifetime total exposure of the mammary gland to the mitogenic effects of ovarian hormones has been proposed to be a major risk factor for the development of breast cancer (MacMahon, B., et al., J. Natl Cancer Inst 50:21–42 (1973)). However, very little is known about the mitogenic effects of estrogen in the postmenopausal human breast.

The mouse has been widely studied in vivo for elucidating roles of hormones in mammary gland development and function, and the mouse mammary gland is similar to the human breast in many aspects of hormonal regulation of cell proliferation (Neville, M. C., et al., The mammary gland development, regulation and function. Plenum Press New York and London 625 (1987)). Most mammals, including mice, maintain their reproductive capacity throughout their entire life and do not experience natural menopause (Kirkwood, T. B. L., Comparative and evolutionary aspects of longevity In: Adelman R., et al. (eds) Handbook of the biology of aging. Van Nostrand Reinhold Co. New York 27–42 (1985)). However, a menopausal state in animals can be induced surgically, by ovariectomy. This is comparable to the situation in women who undergo bilateral ovariectomy prior to menopause, and prematurely experience the symptoms and side effects of menopause soon after surgery. In many instances women start hormone replacement therapy in the early postmenopausal period in order to alleviate menopausal symptoms. However, older postmenopausal women who have never previously received HRT are also given estrogen for its ability to reduce osteoporosis and decrease risk of cardiovascular disease (Michaelsson, K., et al., Br Med J 316:1858–1863 (1997); Prelevic, G. M., et al., Bailliere's Clinical Endocrinology and Metabolism 11:311–340 (1997); Leveille, S. G., et al., J. Am Geriatr Soc 45:1496–1500 (1997); and Miller, K. L., Clin Obst Gynec 39:912–932 (1996)). Thus it was of interest to study the effects of estrogen in early vs. late postmenopause.

In order to counteract the negative side effects of menopause, such as vasomotor and urogenital dysfunction and to reduce osteoporosis and cardiovascular disease, women are prescribed hormone replacement therapy (HRT) with an estrogen (E) or estrogen plus progestin (P) (Hutchinson, T. A., et al., Lancet 2:705–709 (1979); Weiss, N. S., et al., N Engl J Med 303:1195–1198 (1980); Ross, R. K., et al., Lancet 1:858–860 (1981); Stampfer, M. J., et al., N Engl J Med 313:1044–1049 (1985); The writing group of PEPI trial. JAMA 276:1389–1396 (1996); Udoff, L., et al., Obstet Gynecol 86:306–316 (1995). Since the majority of postmenopausal women have an intact uterus, combination or sequential HRT with E and P are most commonly prescribed.

HRT also has negative consequences. Length of lifetime exposure to ovarian hormones has been proposed to be a major risk factor for the development of breast cancer (MacMahon, B., et al., J Natl Cancer Inst 50:21–42 (1973)). Furthermore, in contrast to that ability of P to inhibit E effects in the uterus, P synergizes with E to produce a maximal proliferative response in the mammary gland of the rodent and monkey (Haslam, S. Z., Endocrinology 122:464–470 (1988); Wang, S., et al., Endocrinology 127:2183–2189 (1990); Cline, J. M., et al., Am J Obstet Gynecol 174:93–100 (1996)). We have recently reported that normal breast tissues from postmenopausal women receiving combined HRT with estrogen plus progestin, exhibit significantly higher epithelial cell proliferation and greater epithelial density compared to no HRT or E alone HRT (Hofseth, L. J., et al., J Clin Endocrinol Metab 84:4559–4565 (1999)). Since HRT with E+P is associated with greater proliferation in the postmenopausal breast than E alone, this could have important implications for increased breast cancer risk. This is supported by a recent epidemiological study that found a greater risk of breast cancer in women who received E+P HRT than those who received E alone HRT (Magnusson, C., et al., Int J Cancer 81:339–344 (1999)).

Women usually initiate HRT in the early postmenopausal period in order to reduce menopausal symptoms. However, older postmenopausal women who have never previously received HRT now also receive HRT to reduce osteoporosis and cardiovascular disease. Thus, a new variable, the timing of initiation of HRT in early vs.late postmenopause, also requires evaluation for its effect on breast proliferation.

The murine mammary gland has been widely studied in vivo for elucidating the role of hormones in mammary gland development and function and is similar to the human breast in many aspects or hormonal regulation of cell proliferation (Neville, M. C., et al., The mammary gland development, regulation and function. Plenum Press, New York and London (1987)). Other related art is:

Iizuka, S., et al., Methods and Findings in Experimental and Clinical Pharmacology, V20, N1 (January–February), P39–46 (1998);

Yagi, K., ACTA Biochimica Polonica, V44, N4, P701–709 (1997);

Roux, C., et al., BONE, V19, N5 (November), P463–468 (1996);

Schiffenbauer, Yael S., et al., Proc. Natl. Acad. Sci. USA Vol. 94, pp 13203–13208 (1997);

Jagger, C. J., et al., J. Clin. Invest. Vol. 98, No. 10, 2351–2357 (1996);

Whelton, B. D., et al., Toxicology 119 141–153 (1997);

Wilson, Iain A., et al., European Journal of Pharmacology 381 93–99 (1999);

Whelton, B. D., et al., Toxicology 119 123–140 (1997);

Whelton, B. D., et al., Toxicology 119 103–121 (1997); and

Shimizu, H. et el., Journal of Endocrinology 154 285–292 (1997).

SUMMARY OF THE INVENTION

The present invention relates to a method for determining a response to a biologically active agent in lower laboratory test mammals which comprises:

(a) surgically ovariectomizing the lower mammal at a baseline time;

(b) dividing the ovariectomized lower mammals into at least two groups;

(c) treating a first of the groups of the ovariectomized mammals with the biologically active agent within a first period less than 21 days, from the baseline time;

(d) treating a second of the groups of the ovariectomized mammals with the biologically active agent with a second period of greater than about 35 days from the baseline time;

(e) comparing the results for the first and second groups of mammals to determine the response to biologically active agent.

In particular the present invention relates to mice as the test mammals. The invention approximates early and late menopause in humans.

The biologically active agent can be estrogen alone or in combination with progestin. These agents can be used alone or in combination with other agents which suppress or potentiate their activity. The method can also be used with other compounds which regulate biological activity in females including chemotherapeutic agents including SERMS as described in U.S. Pat. Nos. 5,994,370, 5,395,842, and 5,147,880.

The test mice can be normal or predisposed to a particular disease such as a tumor. All of this is well known to those skilled in the art.

The aim of the present invention is to particularly enable the identification of compounds which positively regulate the effects of estrogen and/or progesterone to prevent disease, such as breast tumors. It is particularly desirable to regulate negative results from estrogen in humans and the present invention enables the simulation of such regulation in a safe and effective manner.

BRIEF DESCRIPTION OF THE DRAWINGS

FIGS. 2A to 2D are photomicrographs of mammary gland wholemounts from mice treated 1 and 5 wk post OVX. Mice received a single ip injection of 1 μg E (a,b) or 0.85% NaCl vehicle control (c,d) at 1 wk (a,c) or 5 wk (b,d) post OVX, and mammary glands were prepared as wholemounts 4 days later. Note the increased size of duct ends present only in the gland treated with E at 5 wk post OVX (b) Magnification 130×.

FIGS. 3A to 3D show histological appearance and proliferative response of duct ends and endbuds in response to estrogen. Adult mice OVX for 5 wk (3A, 3B) received a single ip injection of 1 μg E (3A) or 0.85% NaCl (3B) and were sacrificed 72 h later. Pubertal ovary intact (3C), or OVX (3D) mice. To demonstrate the amount of cell proliferation, all mice were injected with H-thymidine 1 h before sacrifice and tissues processed for DNA histoautoradiography as described in Materials and Methods section. The duct ends (3A) in mammary glands of adult mice treated with E at 5 wk post OVX and the endbuds (3C) in ovary-intact pubertal mice were bulbous, multilayered and contained many DNA-synthetic epithelial cells (dark nuclei). E withdrawal by OVX produced quiescent duct ends (3B) and endbuds (3D) characterized by a single layer of epithelial cells and the lack of DNA synthetic cells in both adult (3B) and pubertal (3D) mice. Magnification 200×.

FIGS. 7A and 7B are graphs showing E-induced proliferation in stromal cells adjacent to or distant from mammary duct ends at 1 or 5 wk post OVX. Mice were OVX (7A) 1 or (7B) 5 wk prior to treatment with E by a single ip injection with 1 μg E or 0.85% NaCl (C). After 72 h, $^3$H-thymidine was injected ip and mammary glands were removed 1 h later and processed for DNA histoautoradiography as described in Materials and Methods. LIs were determined for 50 separate areas that were either adjacent to or distant from (greater than 400 μm away) duct ends. Each bar represents the M±SEM of a minimum of 50 separate areas and a minimum of 2500 cells for each experimental group; n=5 and 9 mice per group at 1 and 5 wk post OVX, respectively. * p=0.001 that E-injected glands had significantly higher LIs than control-treated glands. ** p=0.001 that LI in stromal cells adjacent to duct ends in E-treated glands was significantly greater at 5 wk post OVX than at 1 wk post OVX.

Mice were OVX 1 or 5 wk prior to daily sc injection with 1 μg E or 0.85% NaCl (C) for 28 days. At 24 h after indicated number of daily injections, $^3$H-thymidine was injected ip and mammary glands were removed 1 h later and processed for DNA histoautoradiography as described in Materials and Methods. Control-treated mice were processed at 28 days. LIs for (12A) epithelium and (12B) stromal cells were determined. Each bar represents the M±SEM of values obtained from 1–3 separate experiments with a total of 3–9 mice per time point at 1 and 5 wk post OVX. (12A) * p=0.01–0.05 that LIs for epithelial cells of E-treated mice at 5 wk post OVX, were greater than all control-treated and E-treated mice at 1 wk post OVX. (12B) * p=0.001–0.05 that LIs of stromal cells of E-treated mice at 5 wk post OVX, were greater than all control-treated and E-treated mice at 1 wk post OVX.

FIGS. 13A to 13H are photomicrographs of mammary gland wholemounts from and 1 and 5wk post OVX mice injected with E+P. Adult female mice were OVX 1 (13A, 13C,13E,13G) or 5 wks (13B,13D,13F,13H) prior to daily s.c. injection with E+P (1μg+1 mg) for up to 56 days. Wholemounts from control-injected (13A, 13B) mice are compared with wholemounts after 3 (13C, 13D), 14 (13E, 13F), or 42 (13G, 13H) days of injection. At 3 days the predominant morphological change was enlarged duct ends (13C, 13D) whereas thereafter the predominant morphology is ductal sidebranching and alveolar bud formation. 20× Mag.

Figures 14A, 14B, 14C:
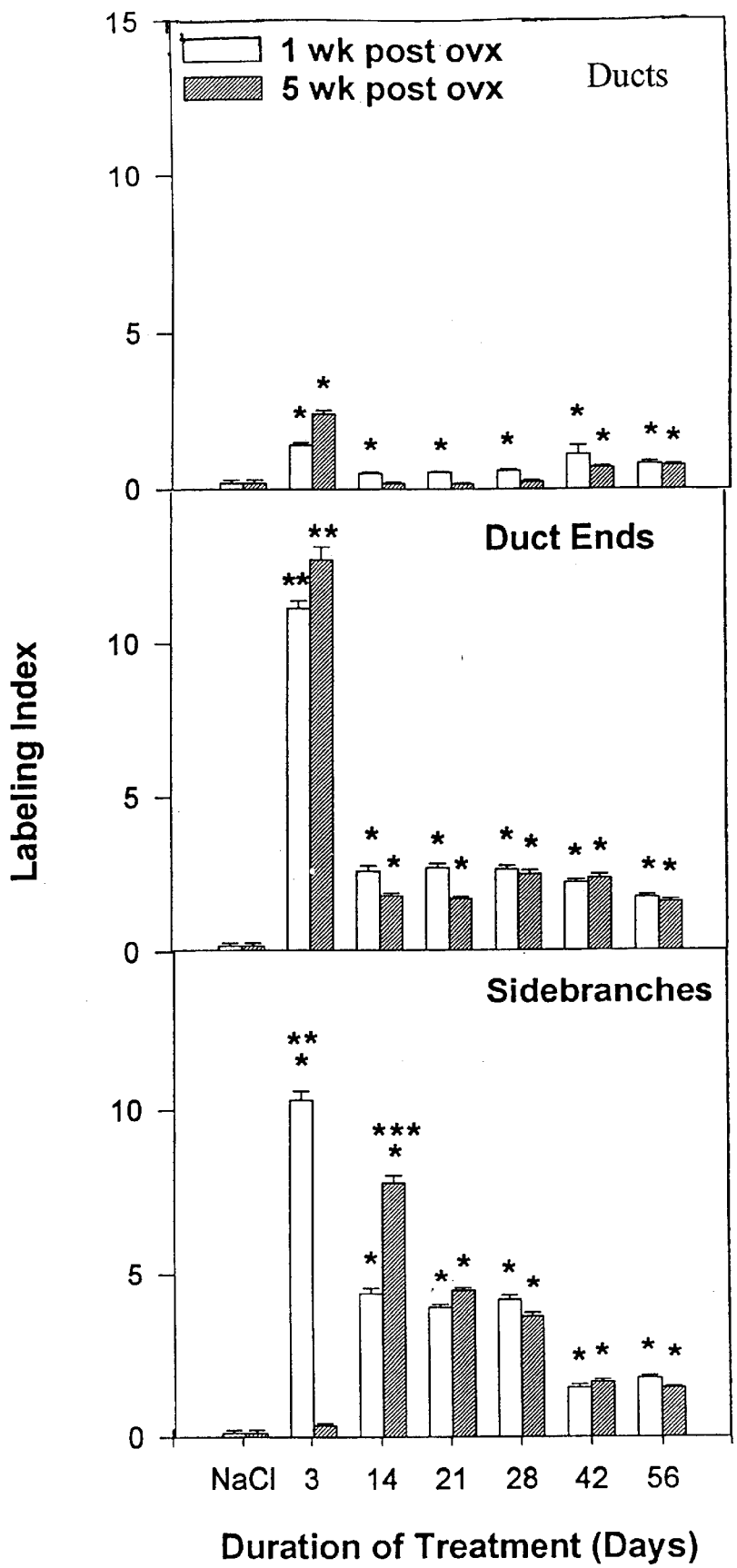

FIGS. 14A to 14C are E+P-induced proliferation of epithelium in ducts, duct ends or side branches at 1 or 5 wk post OVX. Mice were OVX 1 or 5 weeks prior to daily injections with E+P (1 μg+1 mg) for up to 56 days. At indicated times after treatment, $^3$H-thymidine was injected and mammary glands were removed, processed for DNA histoautoradiography, and LIs for epithelial cells determined. Since LIs for control-injected mice never exceeded 0.05% at any time point for both the 1 and 5 wk post OVX control groups, the LIs have been combined for all timepoints for control-injected for each experimental groups. Ducts: * p=0.0001 that LIs for 1 and 5 wk post OVX E+P treated groups are significantly greater than control-treated groups. Duct ends: * p=0.0001 that LIs for 1 and 5 wk post OVX E+P treated groups are significantly greater than control-treated groups;  p=0.0001 that LI for 3 day time point is greater than all other time-points. Sidebranches:  p=0.0001 that 3 day E+P treated 1 wk post OVX group is greater that all other groups; *** p=0.0001 that 14 day E+P treated 5 wk post OVX group is greater than all other time points for 5 wk post OVX mice.

Figures 15A, 15B, 15C:
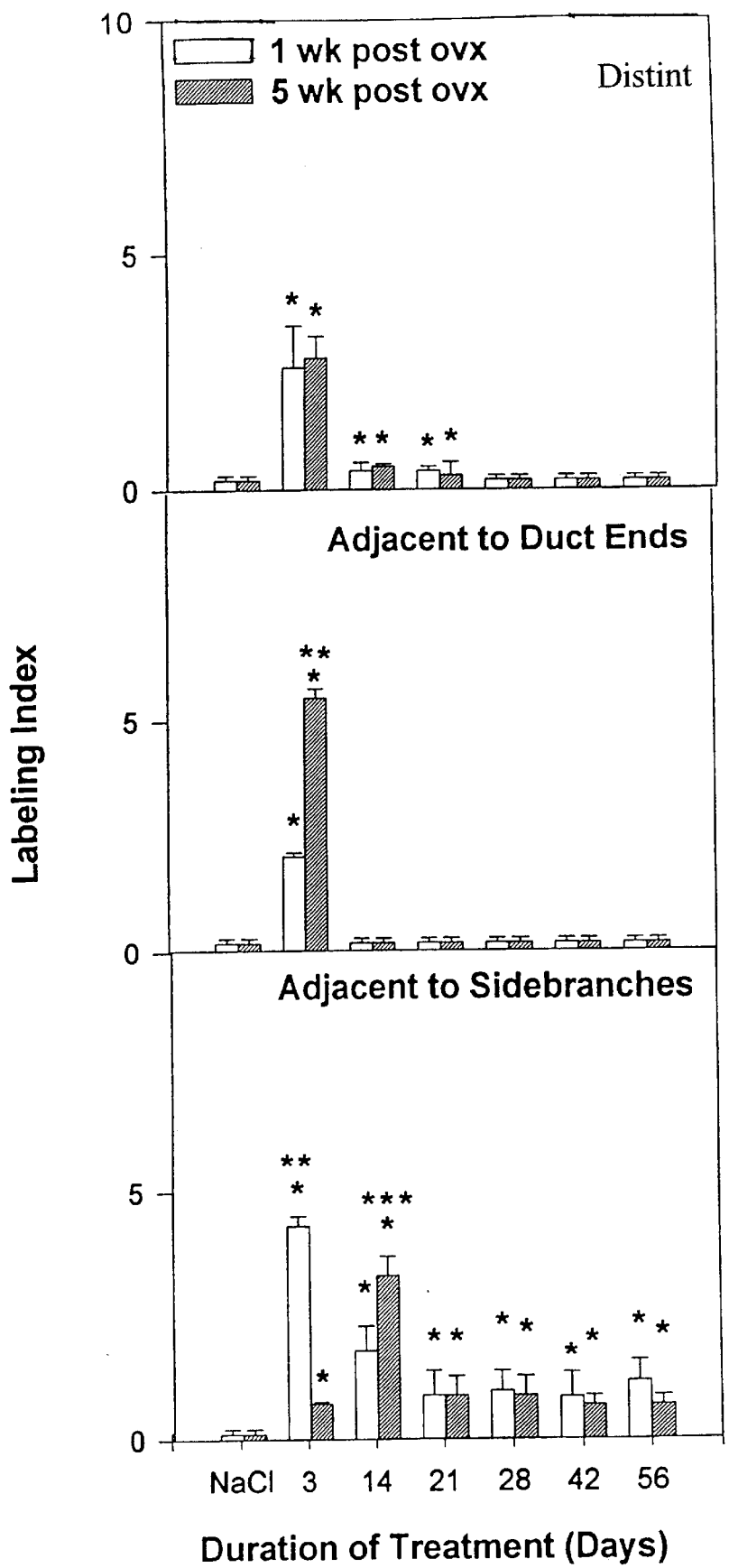

FIGS. 15A, 15B and 15C are E+P-induced proliferation in stroma adjacent to or distant from duct ends or side branches in 1 or 5 wk post OVX. Mice were OVX 1 or 5 weeks prior to daily injections with E+P (1 μg+1 mg) for up to 56 days. At indicated times after treatment, $^3$H-thymidine was injected, mammary glands were removed and processed for DNA histoautoradiography and LI for stromal cells were determined. Since LIs for control injected mice never exceeded 0.05% at any time point for both the 1 and 5 wk post OVX control groups, the LIs have been combined for all time-points for control injected for each experimental groups. Each bar represents the mean±SEM for values obtained from 6 mice per time point per treatment group. Distant: * p=0.0001 that LIs for 1 and 5 wk post OVX E+P treated groups are greater than control groups. Adjacent to duct ends: * p=0.001 that LIs for 1 and 5 wk post OVX E+P treated groups at 3 days are significantly greater than all other groups; ** p=0.0001 that LIs for 5 wk post OVX E+P treated group at 3 days is greater than the 1 wk post OVX E+P-treated group. Adjacent to sidebranches: * p=0.0008–0.01 that LIs for all E+P treated groups are greater than control groups;  p=0.05 that LI for 3 day time point for 1 wk post OVX E+P treated mice is greater than all other time-points; * p=0.002 that 14 day E+P treated 5 wk post OVX mice LI is greater than all other time-points in the same treatment group.

FIGS. 16A to 16F are photomicrographs of mammary glands from 1 and 5 wk post OVX mice treated with RU486 implants and E+P. Mice were OVX 1 (16A, 16C, 1E) or 5 (16B, 16D, 16F) weeks prior to implantation of Elvax pellets containing 0.01 $\mu$g RU486 (16E, 16F); the contralateral mammary gland received control implants (16C, 16D) (* indicates the site of the implant). The implants were followed by 3 daily sc injections with E+P (1 $\mu$g+1 mg). Twenty-four h after last injection, mammary glands were removed and analyzed morphologically. In control-implanted and control-injected mice (no hormone) (16A, 16B), ducts were thin and no enlarged duct ends or sidebranches were visible. In control-implanted glands of 1 and 5 wk post OVX E+P injected mice, duct end enlargement (16C, 16D) and sidebranching was seen (16C). In RU486-implanted glands of 1 wk post OVX, E+P injected mice (16E) there were no enlarged duct ends or sidebranching adjacent to the RU486 implant. In contrast, in RU486-implanted, 5 wk post OVX, E+P injected mice (16F) enlarged duct ends were still visible in the region of the implants. 10× Mag.

Figures 17A, 17B, 17C:
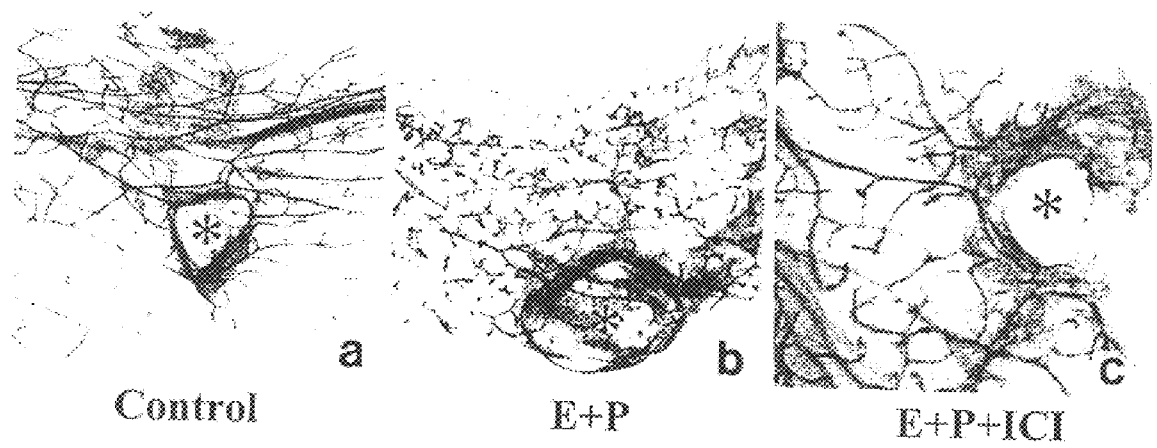

FIGS. 17A to 17C are photomicrographs of mammary glands of 5 wk post OVX mice treated with ICI 182,780 implants and E+P. Mice were OVX 5 weeks prior to implantation of Elvax pellets containing 0.01 $\mu$g ICI 182,780 (17C); the contralateral mammary gland received control implants (17B); (* indicates the site of the implant). The implants were followed by 3 daily sc injections with E+P (1 $\mu$g+1 mg) (17B, 17C) or control-implant and control vehicle injection (17A). Twenty-four hr after last injection, mammary glands were removed and analyzed morphologically. In control-implanted and control-injected mice (17A), ducts were thin and no enlarged duct ends were visible. In control-implanted, E+P-injected mice (17B), duct end were enlarged (17C). In ICI 182,780-implanted, E+P-injected mammary glands (17C) the number of enlarged duct ends adjacent to the implant were significantly reduced. 20× Mag.

Figures 18A, 18B:
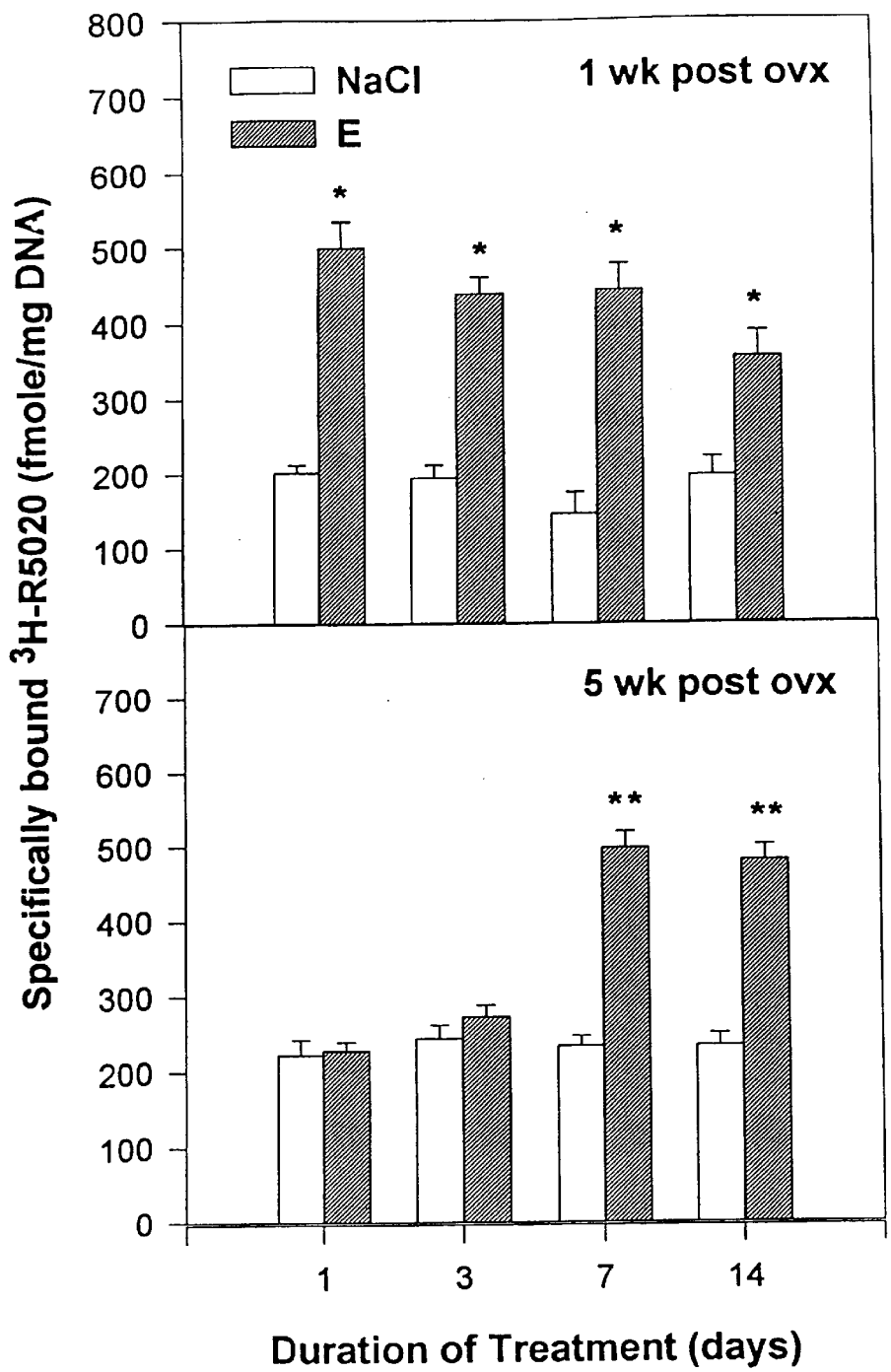

FIGS. 18A and 18B are graphs showing the time course of E induction of PR in 1 and 5 wk post OVX mice. Mice were OVX for 1 or 5 wks prior to daily ip injection with E (1 $\mu$g) for up to 14 days. PR levels were determined by ligand binding assay 24 h after last E injections at the time points indicated. Each value represents the mean±SEM obtained from triplicate values with tissue pooled from 3 mice per time point per treatment group. * p=0.0001 that PR levels in E-treated 1 wk post OVX mice were greater than control-treated mice at all time-points tested. ** p=0.0001 that PR levels in 5 wk post OVX mice at 7 and 14 days were greater than all other 5 wk post OVX treatment and control groups.

DESCRIPTION OF PREFERRED EMBODIMENTS

Hormone replacement therapy (HRT) with estrogen alleviates menopausal symptoms and is effective in reducing osteoporosis and cardiovascular disease when taken in early postmenopause. Older, late postmenopausal women who never previously received HRT are also believed to benefit from estrogen treatment. On the other hand, increased lifetime exposure of the mammary gland to estrogen may increase the risk of breast cancer. The development of suitable experimental animal model systems can advance our understanding of the effects of estrogen and the timing of HRT on the postmenopausal breast. Toward this end, early and late postmenopausal states were induced in mice by short vs. long-term ovariectomy (1 vs. 5 wk) and the effects of 17β-estradiol (E) on mammary gland morphology, cell proliferation and progesterone receptor (PR) levels were investigated. In late postmenopausal mice, E caused a pronounced enlargement of duct ends and a 6.5- and 4-fold greater mitogenic response in the duct end epithelium and adjacent stromal cells respectively, as compared to the response in early postmenopausal mice. Furthermore, after long-term, daily treatment with E, steady-state levels of proliferation remained 2-fold higher than that of similarly treated, early postmenopausal mice. E failed to increase mammary progesterone receptor (PR) levels in late postmenopausal, but not in early postmenopausal mice. Stimulation of duct ends by E and lack of PR-inducibility are characteristics of the immature pubertal mammary gland, and indicate that the late postmenopausal mammary gland resembled the immature state. In contrast, minimal E-induced proliferation and increased PR inducibility, characteristics of the adult, sexually mature mammary gland, were retained in early postmenopausal mice. The lack of difference in the numbers of estrogen receptor (ER) positive epithelial or stromal cells or in ER cellular concentration after short vs. long-term ovariectomy indicate that the observed greater efficacy of E is mediated at a step beyond receptor-ligand binding. This mouse model of experimentally induced early vs. late postmenopausal states should prove useful in better understanding alterations in hormone responsiveness and their implications for timing HRT on the human breast.

Results suggest that altered hormonal milieu and long-term deprivation of ovarian hormones, rather than advanced age are the major contributing factors to the observed differences in response to E alone HRT in the murine model. The purpose of the present study was to examine the proliferative effects of long-term combined treatment with E+P on the mammary gland in a murine model of early and late postmenopause.

EXAMPLE 1

Material and Methods

Chemicals

Unlabeled R5020 and [$^3$H]R5020, a synthetic (17,21-dimethyl-19-nor-4,9-pregna-diene-3,20-dione; S.A., 87.0 Ci/mmol), and unlabeled 17β-estradiol (E) were purchased from New England Nuclear Corp. (Boston, Mass.). [Methyl-$^3$H]thymidine (S.A., 50 Ci/mmol) was purchased from ICN Radiochemical Corp. (Irvine, Calif.). All other chemicals were purchased from Sigma Chemical Co. (St. Louis, Mo.). All other chemicals were reagent grade.

Animals, surgical procedures and hormone administration.

Ten-week-old or 9–12 month-old BALB/c female mice from our own colony were bilaterally ovariectomized (OVX) under Nembutal anesthesia 1 or 5 weeks prior to E treatment. Varying doses of E in 0.85% NaCl were administered by ip or sc injection; in pilot studies results were not significantly different for the two injection routes. Injection was chosen as the method of systemic administration to optimize precision and reproducibility of hormone dosage. Serum levels of E were determined after OVX and E injection by radioimmunoassay using a commercial kit (Diagnostic Products Corp., Los Angeles, Calif.) according to the suppliers instructions. Time course studies revealed that after E injection, maximal DNA synthesis and morphological responses were observed at 72 h and 96 h, respectively. Therefore, in all experiments except time course studies, mammary glands were analyzed at 72 h after E treatment for DNA histoautoradiogrpahy and at 96 h after E treatment for morphological analysis.

DNA Histoautoradiography

At various times after E injection, animals received a single ip injection of [$^3$H]thymidine in a dosage of 2 $\mu$Ci/g BW 1 h before sacrifice. The mammary glands were removed, fixed and processed as wholemounts followed by embedding and sectioning for histoautcradiographic analysis as described previously. Histological sections were examined at 400× magnification to determine the DNA labeling indices (LIs) of epithelial and stromal cells. In view of the stimulatory effect of E on duct ends, epithelial cell LIs were also quantitated separately in ducts vs. duct ends. In parallel, stromal cell LIs were determined for areas adjacent to and distal from duct ends. Adjacent areas were defined to be within 400 pm of the duct end (i.e. in the same microscope field at 400× magnification) and the distal areas were defined to be more than 400 $\mu$m away from the duct end. A minimum of 10 individual structures were evaluated for each of 5–9 mice per experimental group. Determination of LI was facilitated by the use of a computer-interfaced morphometric digitizing system as described previously (Haslam, S. Z., Endocrinol 122:464–470 (1988)).

Steroid Hormone Binding Assay

To determine PR concentration, cytoplasmic extracts were prepared separately for mammary gland and uteri as described previously (Haslam, S. Z., et al., Endocrinol 108:825–830 (1981)). Mammary gland and uterine cytoplasmic extracts were incubated with a single saturating concentration of 20 nM [$^3$H]R5020 with 100-fold excess radioinert dexamethasone (for suppression of progestin binding to glucocorticoid receptors) or with 100-fold excess radioinert R5020. Specific binding was determined using a dextran-coated charcoal assay procedure as previously described (Haslam, S. Z., et al., Endocrinol 108:825–830(1981)). Tissue DNA was quantitated as previously described (Ceriotti, G., J Biol Chem 198:297–303 (1952)).

ER Immunohistochemistry

The immunohistochemical procedure was carried out on frozen sections of mammary tissue using anti-ER monoclonal antibody, H222 (10 $\mu$g/ml) (gift of Abbott Labs (Abbott Park, Ill.), and was used as described previously (Haslam, S. Z., et al., J Steroid Biochem Molec Biol 42:589–595 (1992)). To quantitate the number of ER positive cells by light microscopy, 3,3'-diaminobenzidine tetrahydrochloride chromogen substrate was used and quantitation of the percentage of ER positive cells was facilitated by the use of a computer-interfaced morphometric digitizing system (Haslam, S. Z., et al., J Steroid Biochem Molec Biol 42:589–595 (1992)). To quantify the amount of ER per cell, the same immunohistochemical procedure was carried out as above, except that ER antibody was visualized in tissue sections after incubation with a fluorescein-conjugated, goat anti-rat (1:36 dil; 45 min at 20° C.) secondary antibody (Cappel Res. Prod., Durham, N.C.). Fluorescently labeled sections were mounted onto slides with Slow Fade (Molecular Probes, Eugene, Oreg.) and analyzed under an Odyssey Laser Scanning Confocal Microscope (Noran Instruments, Inc., Madison, Wis.). The confocal microscope was equipped with Image-1 Software (Universal Imaging Corp., Pennsylvania) which allows the image storage and fluorescence intensity measurements as described previously (Ankrapp, D. P., et al., J Cell Physiol 174:251–260 (1998)). For fluorescein, the excitation and primary barrier filters were 488 and 515 nm, respectively. A 40× objective was used for capturing images, and the binding of anti-ER antibody was quantified using the function "Brightness Measurement: Area Brightness" of the Image-1. The amount of ER in antibody-treated sections was determined by quantitating the intensity of fluorescence staining. To determine the intensity of fluorescence staining, individual cells were outlined using the "Area Brightness" function and the average pixel brightness within the circumscribed areas that was due to anti-ER antibody staining was calculated by the Image-1 program. For anti-ER staining, the background level of fluorescence obtained with normal serum in parallel control sections was subtracted from fluorescence intensity obtained with anti-ER antibody. In all cases images were captured and stored by 24 h after antibody treatment in order to reduce variability due to fluorescence fading. There were no significant differences in fluorescence measurements between sections from the same treatment groups.

Statistical Analysis

All data are expressed as the mean±SEM and were analyzed for significance using the Student t-test or analysis of variance as appropriate. The p value chosen for significance was $\leq 0.05$.

Results

Effect of Time After Ovariectomy and Age on E-responsiveness

Figures 1A, 1B:
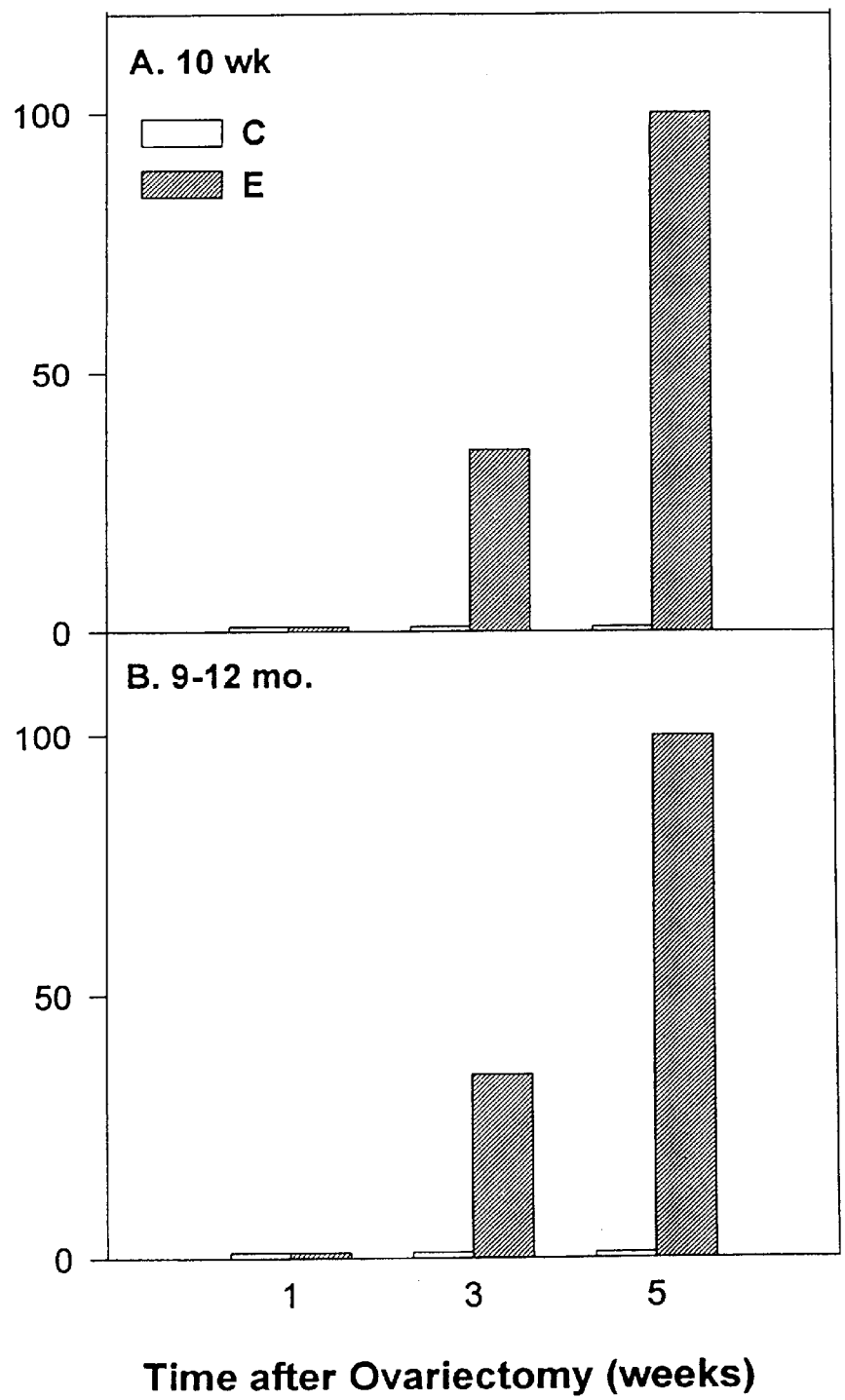
FIGS. 1A and 1B are graphs showing effect of time after ovariectomy on E-induced changes in mammary gland morphology in 10-week-old and 9–12-month old mice. (1A) 10-week-old or (1B) 9–12-month-old mice were OVX for indicated lengths of time prior to a single ip injection with 1 μg estradiol (E) or 0.85% NaCl vehicle control (C) Four days later the mammary glands were prepared as wholemounts and analyzed for changes in morphology. Each bar represents the percentage of mammary glands that exhibited enlarged duct ends, with 8 mice per time point, for each age group.

In adult mice, endogenous serum estradiol reaches baseline levels by 24–48 h post OVX (Nelson, J. F., et al., Biol Reprod 24:784–794 (1981)). The shortest period of time previously used for the mammary gland to achieve a baseline against which responses to exogenously administered E could be measured and for mice to recover from surgery was 1 wk post OVX (Haslam, S. Z., Endocrinol 122:464–470 (1988); Haslam, S. Z., et al., Endocrinol 108:825–830 (1981); Haslam, S. Z., et al., J Steroid Biochem Molec Biol 42:589–595 (1992); and Ankrapp, D. P., et al., J. Cell Physiol 174:251–260 (1998)). Thus 1 wk post OVX was selected as an experimental approximation of an early postmenopausal state. In order to analyze mammary gland response in a simulated early vs. late postmenopausal state, the morphological response to E treatment of adult mice was assessed at varying times post OVX. FIG. 1A shows that the percentage of the mammary glands exhibiting a morphological response after E treatment increased with increasing length of time after OVX with 100% of the glands exhibiting stimulation of duct ends in animals at 5 wk post OVX. In 1 and 5 wk post OVX control-injected mice, mammary gland morphology was identical and was characterized by simple ducts lacking significant sidebranching and alveolar buds (FIGS. 2c,d). E treatment at 1 wk post OVX had no effect on morphology (FIG. 2a). However, E treatment at 5 wk post OVX produced enlarged duct ends (FIG. 2b). Histological analysis of the enlarged duct ends revealed the presence of multiple layers of epithelial cells (FIG. 3a). These enlarged duct ends were similar in appearance to endbuds growing in response to endogenous E in mammary glands of ovary-intact, immature pubertal mice (FIG. 3c). Endbuds are the epithelial structures that exhibit the highest degree of proliferation and are major growth points leading to ductal elongation during puberty. Estrogen withdrawal by OVX in both immature and adult mice produced quiescent duct ends characterized by a single layer of epithelial cells and a reduced number of DNA synthetic cells (FIGS. 3b,d).

Menopause results in the loss of ovarian function in humans, but also occurs with advanced age, with a mean age at menopause of 50 years (Speroff, L., et al., The ovary from conception to senescence In: Brown, C. L. (Ed) Clinical gynecologic endocrinology and infertility Williams & Wilkins, Baltimore, Md. 121–163 (1989)). The average life-span of the laboratory mouse is about 2 years, thus 12 months is roughly equivalent to middle age in the mouse. In order to include the age component in reproducing a postmenopausal status in mice, 9–12 month old animals were also OVX at 1, 3 or 5 weeks prior to E treatment. As can be seen in FIG. 1b, the extent of the stimulatory response to E as a function of time after ovariectomy was identical to that obtained in 10-week-old mice. Furthermore, the morphological response was also identical (data not shown). Because length of time after ovariectomy rather than age was the major determining factor of the extent of the E response, in the interest of reducing the time and cost required for these studies, all further experiments were carried out using 10-week-old mice. Mice OVX 1 wk or 5 wk prior to E treatment were chosen to represent early and late postmenopausal states, respectively, in this study.

Sex steroid hormones are also produced by the adrenal glands. One possible explanation for the enhanced response to E observed with increasing time after ovariectomy was a compensatory increase in circulating E derived from adrenal gland biosynthesis. This did not appear to be a likely explanation based upon the persistent attenuated ductal morphology observed at 5 wk post OVX. However, to address the question of adrenal hormone contribution directly, the study was repeated in mice that were ovariectomized plus adrenalectomized. The morphological and DNA synthesis results obtained were identical to those obtained with ovariectomy alone (data not shown), ruling out a significant adrenal contribution to the E response observed at 5 wk post ovariectomy.

Time course and Dose Response of E-induced Cell Proliferation

Figures 4A, 4B:
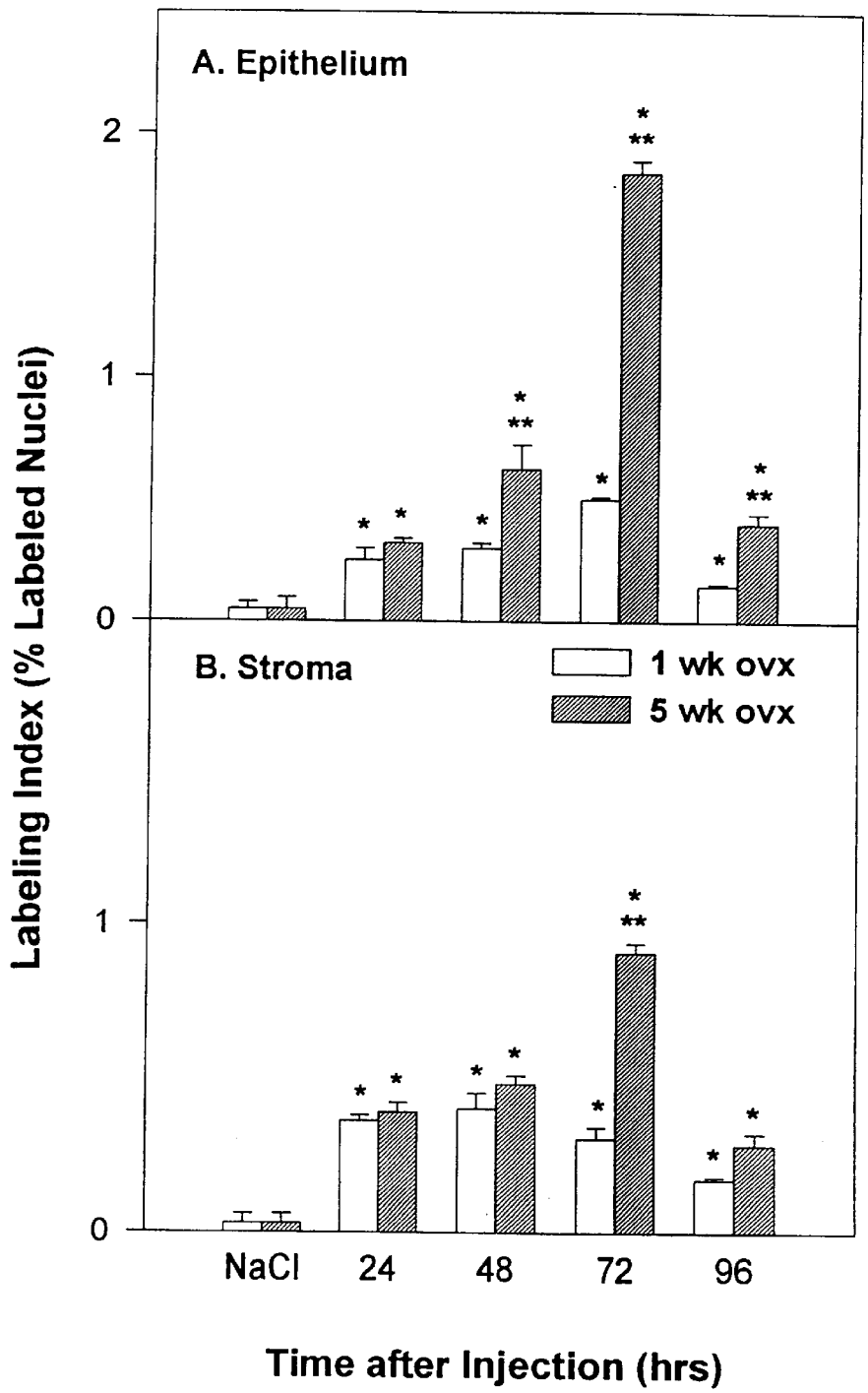
FIGS. 4A and 4B are graphs showing time course of DNA synthesis in mammary epithelial and stromal cells after treatment with E at 1 vs 5 wk post OVX. Mice were OVX 1 or 5 wk prior to a single ip injection of E (1 μg) or 0.85% NaCl. At indicated times after treatment, $^3$H-thymidine was injected ip and mammary glands were removed 1 h later and processed for DNA histoautoradiography as described in Materials and Methods. Labeling indices (LIs) for (4A) epithelial and (4B) stromal cells were determined. Each bar represents the M±SEM of values obtained from 5–6 mice per time point in each experimental group. Since the LIs never exceeded 0.05% at any time point for both the 1 and 5 wk OVX control groups, the LIs for control injected mice have been combined for all time points for each experimental group. * p=0.05 that LIs in E-injected glands was significantly greater than LIs of control injected glands. **p=0.01 that LIs of E-treated glands was significantly greater at 5 wk post OVX than at 1 wk post OVX.
Figures 5A, 5B:
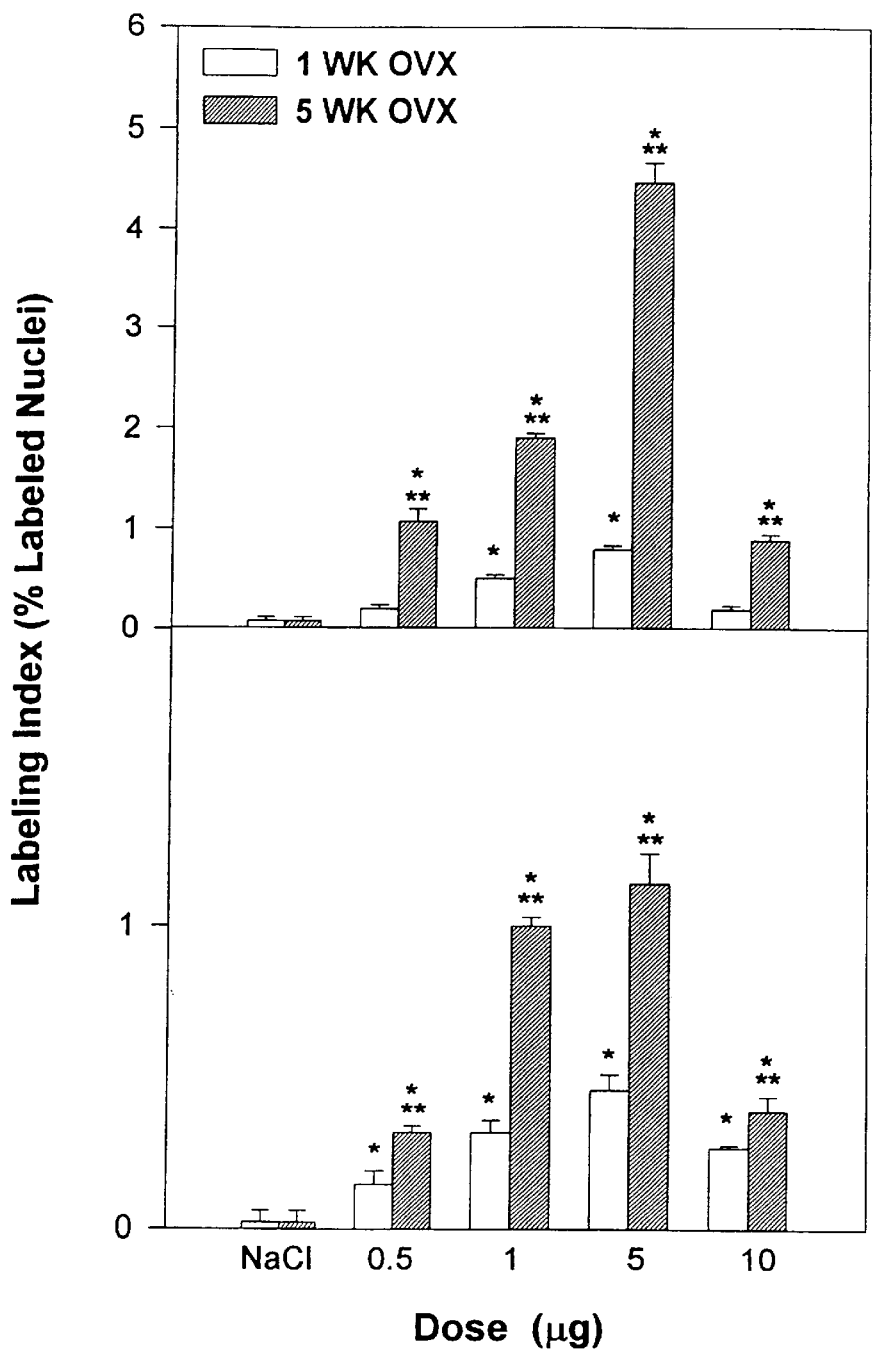
FIGS. 5A and 5B are graphs showing estrogen dose response of mammary epithelial and stromal cell proliferation at 1 vs 5 wk post OVX. Mice were OVX 1 or 5 wk prior to injection with varying doses of E or 0.85% NaCl. After 72 hr, $^3$H-thymidine was injected ip and mammary glands were removed 1 h later and processed for DNA histoautoradiography as described in Materials and Methods. LIs for (5A) epithelial and (5B) stromal cells were determined Each bar represents the M±SEM of values obtained from 5–6 mice per dose in each experimental group. Since the LIs never exceeded 0.05% at any time point for both the 1 and 5 wk OVX control groups, the LIs for control-injected mice have been combined for all time points for each experimental group. * p=0.05 that all E-treated glands had a higher LIs than control-treated glands. ** p 0.01 that all E-treated glands at 5 wk post OVX had a higher LIs than E-treated glands at 1 wk post OVX

A time course study revealed that the maximal proliferative response in mammary epithelial cells and stromal cells occurred at 72 h after E injection (FIG. 4). In order to determine if the enhanced proliferative response to E at 5 wk post OVX was due to an increase in E potency or due to an increase in E efficacy, a dose response study was carried out (FIG. 5). The maximum proliferative response observed at 5 wk post OVX was 5.6- and 2.5-fold greater than at 1 wk post OVX for epithelial cells and stromal cells, respectively. The ED 50 at 1 and 5 wk post OVX were identical, indicating that the potency of E was the same in the two groups. By contrast, the response to E was significantly greater at 5 wk post OVX than at 1 wk post OVX. Thus, these results indicate that the increase in E-induced proliferation observed at 5 wk post OVX was due to an increase in E efficacy rather than potency. At 1 and 5 wks post OVX basal serum levels of E were 5.4±0.7(n=7)and 5.4±0.5 pg/ml (n=8), respectively. Injection of 1 µg E at 5 wks post OVX resulted in an E serum level of 31±7.8 pg/ml (n=4) at 24 h after injection. This serum E level was similar to that of ovary intact mice (25 pg/ml on day 1 of the estrus cycle) (Nelson, J. F., et al., Biol Reprod 24:784–794 (1981)). Thus, in the interest of using a physiological dose of E, all subsequent studies were conducted using 1 µg E.

Topographical Analysis of E-induced Proliferation in Relation to Specific Mammary Gland Structures Since E-treatment produced a pronounced stimulation in the duct ends at 5 wk post OVX, it was of interest to obtain a better understanding of the proliferative effects of E on specific mammary gland structures. To accomplish this, labeling indices (LIs) were determined individually for duct ends vs. subtending ducts. In parallel, stromal cell LIs were determined for cells adjacent to vs. distal from duct ends. When LIs were analyzed in this way (FIG. 6) there was a 6.5-fold higher E-induced stimulation of DNA synthesis in duct ends at 5 wk post OVX than at 1 wk post OVX. Furthermore, little or no DNA synthesis was observed in ducts. Analysis of stromal cell LIs (FIG. 7) revealed a 4-fold higher stimulation of DNA synthesis in the stromal cells immediately surrounding the enlarged duct ends at 5 wk post OVX vs. stroma adjacent to the quiescent duct ends at 1 wk post OVX. These results indicate that there is a paracrine interaction between proliferating duct end epithelium and nearby stroma which occurs only over a short distance.

Estrogen Receptor Levels

Figures 8A, 8B:
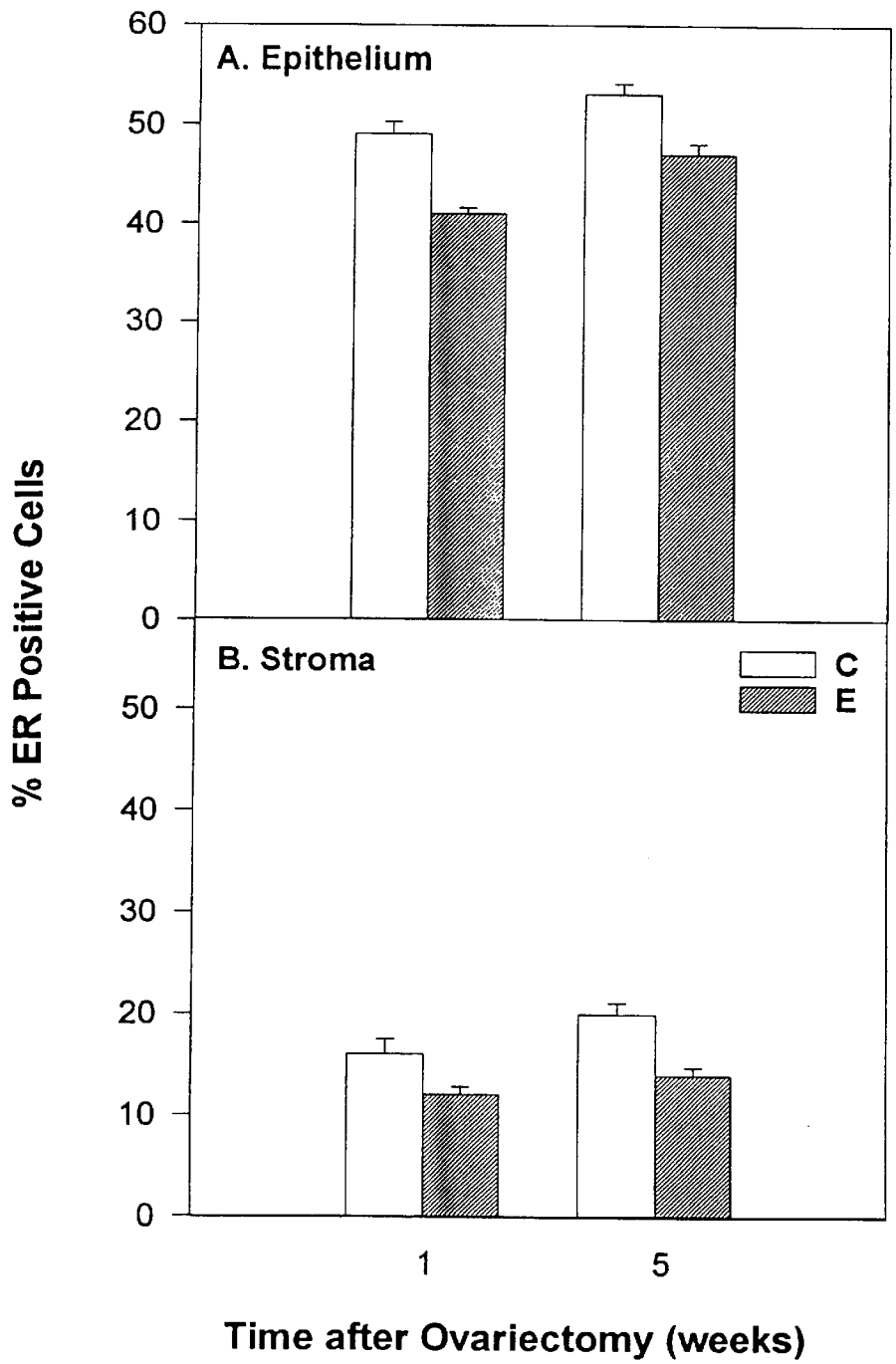
FIGS. 8A and 8B are graphs showing cellular distribution and percentage of ER positive cells in control and E-treated mice at 1 vs 5 wk post OVX. Mice were OVX 1 or 5 wk prior to a single ip injection with 1 μg E or 0.85% NaCl (C). After 24 h, mammary glands were removed and processed for ER by immunohistochemistry. ER positive cells in (8A) mammary epithelium and (8B) stroma were quantitated as described in Materials and Methods. Each bar represents the M±SEM of a minimum of 6000 cells for each experimental group, n=6 mice for each treatment group.

The increased efficacy of E could be due to an increase in estrogen receptor (ER) concentration; therefore ER content of the mammary glands was analyzed. Since estrogen is believed to stimulate mammary epithelial proliferation indirectly via a paracrine mechanism as the result of estrogen action on nearby ER positive mammary stromal cells (Cunha, G. R., et al., J Mammary Gland Biol Neoplasia 2:393–402 (1997); and Haslam, S. Z., et al., Endocrinol 129:2017–2023 (1991)), ER content was determined separately for the epithelial and stromal cell compartments by immunohistochemical analysis. FIG. 8a shows that there was no difference in the percentage of ER positive epithelial cells in control-treated mice at 1 and 5 wk post OVX. Similarly there was no significant difference in the percentage of ER positive stromal cells in control-treated mice at 1 and 5 wk post OVX (FIG. 8b). However, the percentage of ER positive stromal cells was only about 50% that of ER positive epithelial cells. Because of the proposed role of stromal cells to mediate E-induced epithelial proliferation, we also quantitated the percentages of ER positive stromal cells, either adjacent to or distant from duct ends, at 1 and 5 wks post OVX. ER positive stromal cells were evenly distributed throughout the mammary gland and no significant differences were observed between the 1 and 5 wk post OVX groups in either control or E-injected mice (data not shown). At 24 h after E injection, the percentages of ER positive epithelial and stromal cells were significantly decreased at both 1 and 5 wk post OVX, indicative of ER downregulation by E.

Figures 9A, 9B:
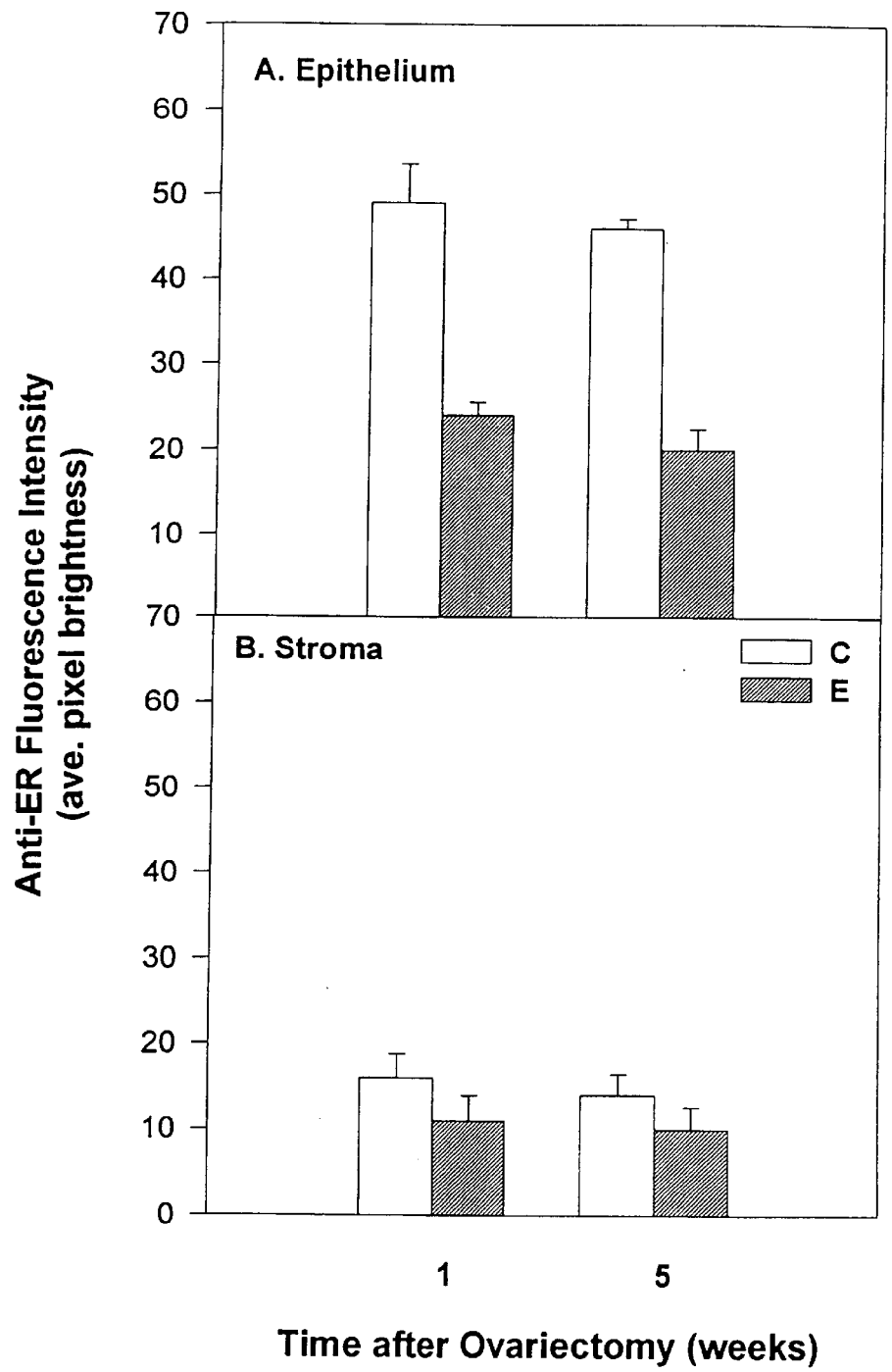
FIGS. 9A and 9B are graphs showing the ER cellular content in mammary cells at 1 vs 5 wk post OVX. Mice were OVX 1 or 5 wk prior to ip injection with 1 μg E or 0.85% NaCl (C). After 24 h, mammary glands were removed and processed for ER by immunohistochemistry using a fluorescein-conjugated secondary antibody for the detection system. ER was quantitated in (9A) mammary epithelium and (9B) stroma as described in Materials and Methods. Each bar represents the M±SEM of a minimum of 6000 cells for each experimental group, n=6 mice for each treatment group.

Although the percentages of ER positive epithelial or stromal cells were not significantly different at 1 vs. 5 wk post OVX, it was possible that ER concentration per cell was different between the two groups. To address this question, immunohistochemical analysis of ER was carried out using a fluorescein-conjugated secondary antibody detection system. This allowed the quantitation of fluorescence intensity as a measure of ER concentration per cell. Analysis of ER cellular content by this method showed no differences at 1 vs. 5 wk post OVX in either epithelial or stromal cells (FIGS. 9 a,b). Decreased cellular ER content was also observed in both epithelial and stromal cells after E treatment.

Estrogenic Regulation of PR Levels

Figure 10:
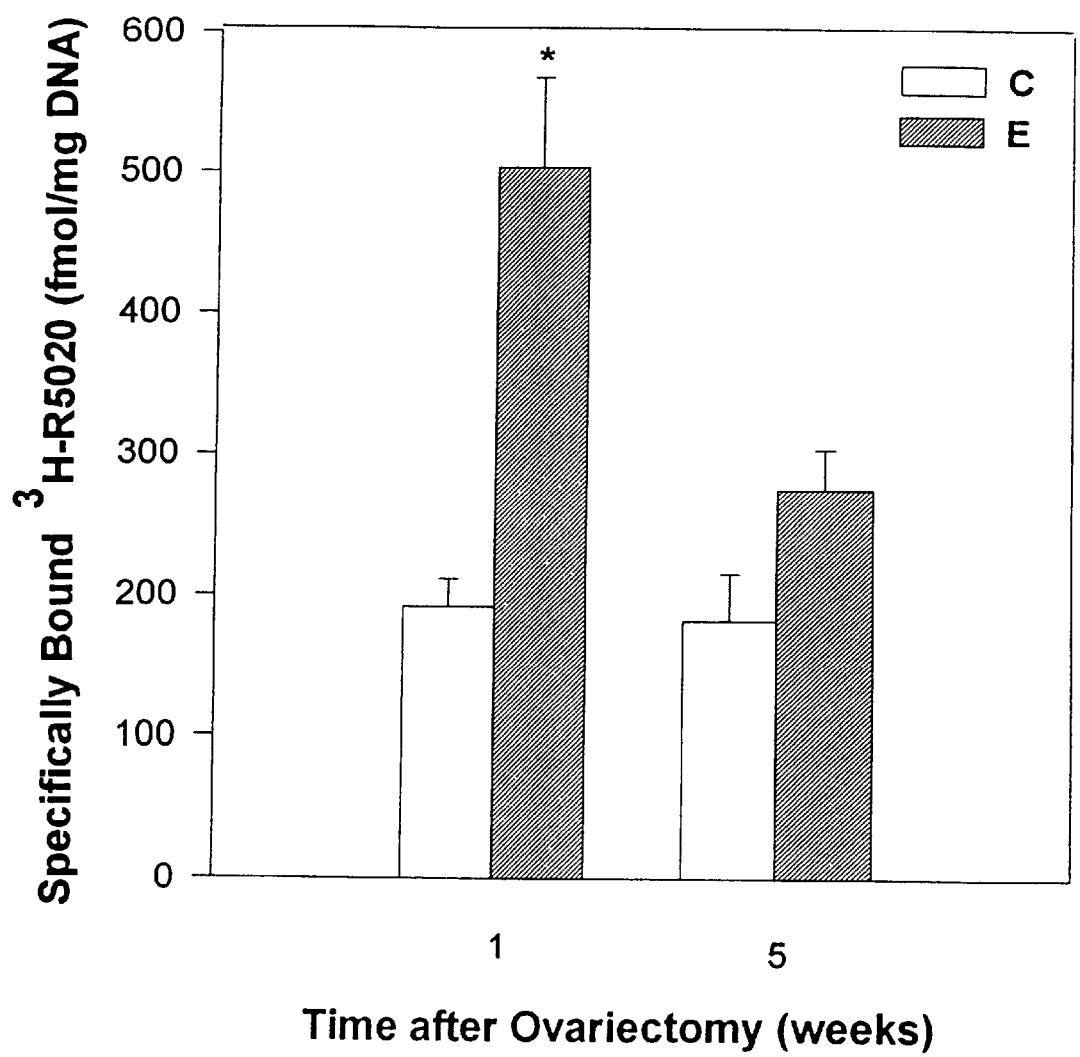
FIG. 10 is a graph showing the effect of E injection on mammary gland PR concentration at 1 vs 5 wk post OVX. Mice were OVX 1 or 5 wk prior to a single ip injection with 1 μg E or 0.85% NaCl (C). At 24 h after injection mammary glands were removed and assayed for specific [$^3$H]R5020 binding as described in Materials and Methods. Each bar represents the M±SEM of 3 experiments; each treatment group contained a total of 9 mice. * p=0.002 that PR binding in E-treated mice at 1 wk post OVX was greater than PR binding in control and E-treated mice at 5 wk post OVX.
Figures 11A, 11B:
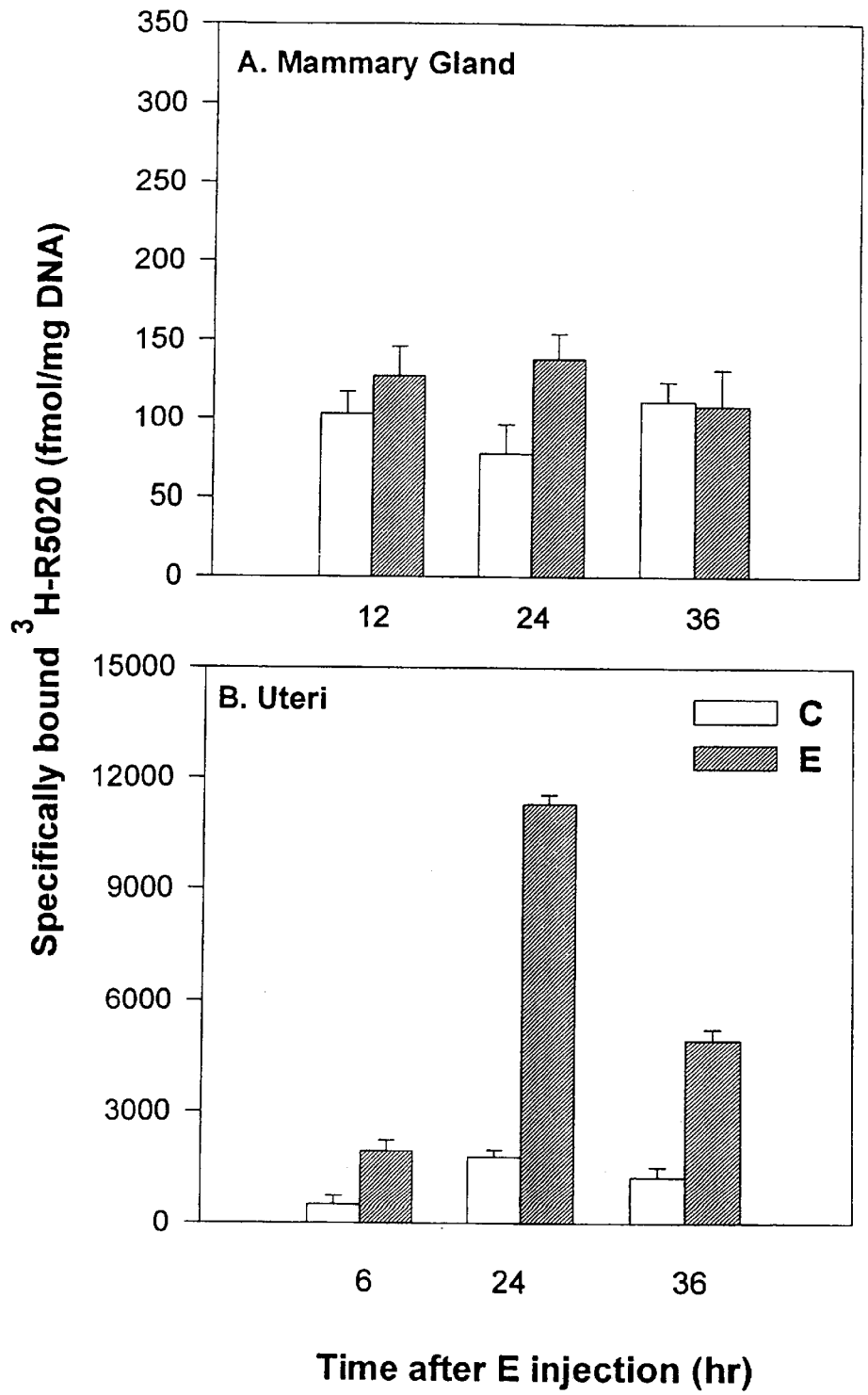
FIGS. 11A and 11B are graphs showing the time course of E-induced increase in PR binding levels in the mammary gland and uterus at 5 wk post OVX. Mice were OVX 5 wk prior to a single injection with 1 μg E or 0.85% NaCl (C). At indicated times after injection (11A) uteri and (11B) mammary glands were removed and assayed separately for specific [$^3$H]R5020 binding as described in the Methods section. Each bar represents the M±SD from two experiments; each time point contained 4–8 mice per experiment.

Another end-point of estrogen action in the adult mammary gland is increased epithelial cell PR levels (Haslam, S. Z., et al., Endocrinol 108:825–830 (1981)). Since long-term OVX conferred an increased proliferative response to E, it was of interest to determine if E-treatment produced a similar enhanced effect on PR regulation. When specific [$^3$H]R5020 binding was measured at 24 hr after E injection, a 2.5-fold increase in PR binding was obtained at 1 wk post OVX (FIG. 10). In contrast, no significant increase in PR binding was observed at 5 wk post OVX. To determine if the lack of increase in PR was due an altered time-course of PR induction at 5 wk post OVX, PR levels were measured at 12, 24 and 36 h after E injection (FIG. 11a). No increase in PR was observed at 5 wk post OVX over the entire time-period tested. The lack of PR induction in mammary glands was not due to a overall lack of E responsiveness at 5 wk post OVX, since an 8-fold increase in PR was observed in the uteri of the same mice at 24 hr after injection (FIG. 11b).

Effects of Long-term E Treatment

Figures 12A, 12B:
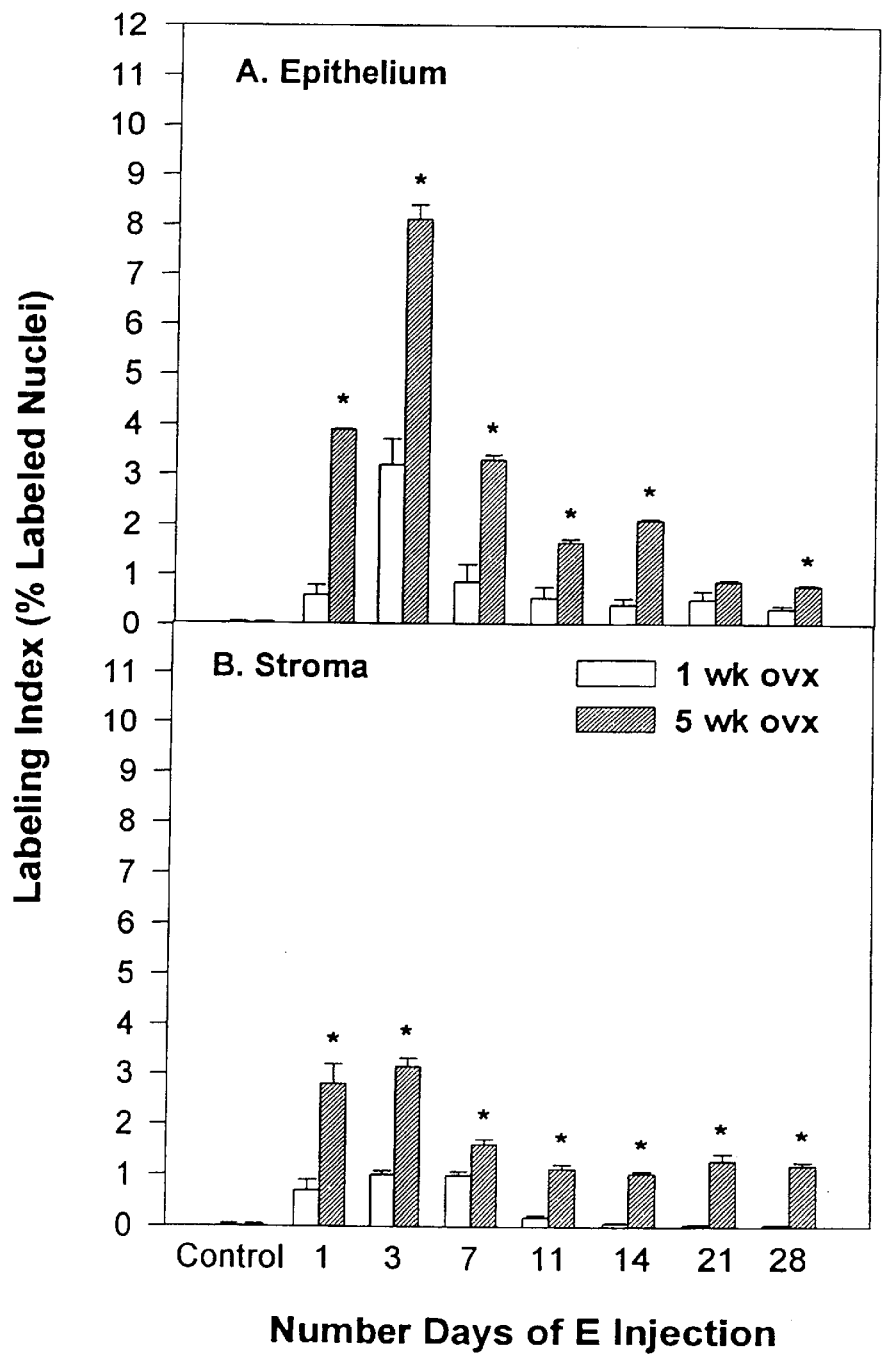
FIGS. 12A and 12B are graphs showing the E-induced proliferation in mammary epithelial and stromal cells during long-term treatment at 1 vs 5 wk post OVX.
Figures 13A, 13B, 13C, 13D, 13E, 13F, 13G, 13H:
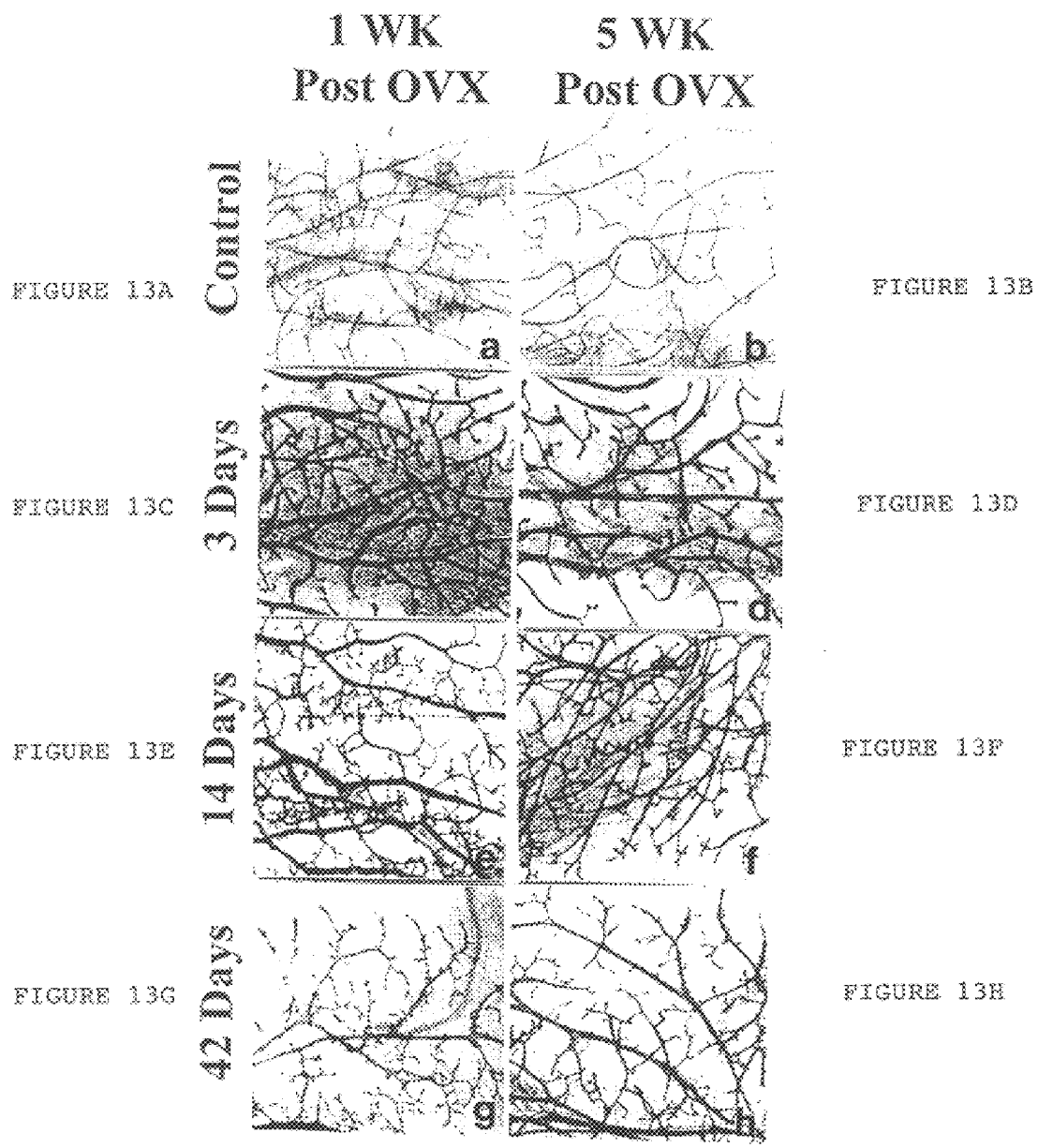

Since women often take HRT for long periods of time, it was of interest to analyze the proliferative response of the mammary glands starting at 1 and 5 wk post OVX to long-term, continuous treatment with E. To accomplish this, E or saline was injected sc daily for up to 28 days. As can be seen in FIG. 12a, the maximal proliferative response in the epithelial cells at 5 wk post OVX was observed after 3 days of E injection, and was 2.6-fold higher than that at 1 wk post OVX. The epithelial cell proliferative response decreased to a steady state level of proliferation but remained 2.3-fold higher than that started at 1 wk post OVX. After 3 days of E injection at 5 wk post OVX the mammary gland contained enlarged duct ends similar to that observed at 96 h after a single E injection. As a steady state LI was reached at 11–14 days, the duct ends remained enlarged, but contained fewer $^3$H-thymidine labeled cells (data not shown). A similar pattern of increased proliferative response to E was also seen in mammary stromal cells at 5 wk post OVX. The increased steady-state proliferative response to E in both mammary epithelial and stromal cells when continuous, long-term E treatment was started at 5 wk post OVX indicates that long-term OVX confers a permanent alteration in mammary gland responsiveness to E.

Discussion

In this paper we have examined the effects of E treatment at an early time (1 wk) vs. at a late time (5 wk) post OVX on mammary gland morphology, cell proliferation and PR regulation. We view this study as a model for understanding the effects of HRT with E in an early vs. late postmenopausal mammary gland. The novel findings from our studies demonstrate that a postmenopausal state produced by long-term ovariectomy conferred an enhanced proliferative response to E which was characterized morphologically by a pronounced hyperplasia of duct ends. This increased mitogenic response to E was localized to the epithelium of these duct ends and nearby stromal cells and resulted in a 6.5-and 4-fold increased LI in this epithelium and stroma, respectively. Long-term E treatment produced a lower steady state proliferative response. However both epithelial and stromal cell proliferation was 2-fold higher when long-term E treatment was started at 5 wk post OVX vs. 1 wk post OVX. Thus, there was an apparent permanent enhanced proliferative response to E after long-term OVX. By contrast, no morphological response and minimal epithelial and stromal cell proliferation were observed after any length of E treatment of short-term OVX, early postmenopausal mice. Analysis of age vs. length of time after ovariectomy on mammary gland response revealed that the enhanced proliferative response was determined by length of time after ovariectomy.

The time points, 1 and 5 wks post OVX appear to be appropriate choices to represent early and late postmenopausal states, respectively. Our results show that 1 wk post OVX is the shortest period of time required by the adult mammary gland to achieve a baseline against which a response to exogenously administered E can be measured. While serum levels are reduced to baseline in adult mice 2–3 days after OVX, our data in FIG. 4 show that after a single injection of 1 μg E, cell proliferation was not reduced to a baseline level by 4 days. However, by 1 wk post OVX, basal levels of proliferation were reached for both mammary epithelium and stroma and were not further decreased with increasing time up to 5 wks post OVX (FIG. 4). Furthermore, morphological and histological evidence demonstrate that the mammary glands of 1 wk OVX mice were regressed compared to the ovary intact state (FIGS. 2, 3). Thus the time period of 1 wk post OVX is a reasonable time point to choose for the early postmenopausal state. We have since also carried out studies in mice at 10 and 15 wks post OVX and have observed estrogenic stimulation of duct ends at these time points (unpublished observations, Raafat & Haslam). Thus, the use of 5 wks post OVX appears to be an appropriate time point for the late postmenopausal state and exhibits the responses to E that are also observed at much longer times post OVX.

The enlarged duct ends obtained in response to E in long-term OVX mice were similar in histological appearance to endbuds of immature pubertal mice (see FIG. 3). Endbuds are the epithelial structures that exhibit the highest degree of proliferation and are major growth points leading to ductal morphogenesis during puberty. Analysis of E-regulation of PR revealed that there is also a lack of PR inducibility at 5 wk post OVX. The presence of enlarged duct ends in the form of endbuds, and lack of PR inducibility in response to E-treatment are characteristic features of the mammary glands of immature, pubertal mice. The present results indicate that long-term OVX can produce these characteristics of the immature gland in adult mice. This observation is of particular interest with regard to mammary gland susceptibility to carcinogenesis since it is well established that the mammary glands of immature, pubertal mice and rats are the most susceptible to carcinogen-induced mammary tumorigenesis (Russo, I. H., et al., J Mammary Gland Biol Neoplasia 3:49–61 (1998)). Thus it will be of great interest to determine the influence of long-vs. short-term OVX and E replacement on susceptibility to mammary tumorigenesis.

The results of dose response studies lead us to conclude that enhanced E responsiveness may be at least in part due to an increased efficacy of E. Recent studies utilizing mammary tissue recombinants in ER knockout mice have provided compelling evidence in the mouse that the proliferative effect of E in epithelial cells is indirect and requires the presence of ER in mammary stroma (Cunha, G. R., et al., J Mammary Gland Biol Neoplasia 2:393–402 (1997)). In light of these findings, it was important to determine numbers of ER positive cells and cellular ER content separately for the epithelium and stroma. The results of immunohistochemical analysis of mammary gland ER content revealed that the percentages of ER positive cells and ER cellular content was not significantly different in short vs. long-term OVX mice for either epithelial or stromal cells. Thus, increased efficacy of E at 5 wk post OVX does not appear to be due to increased ER content in either the epithelial or stromal cell compartments and this suggests that amplification of the E response occurs at a post receptor-ligand binding step(s).

In addition to the enhanced mitogenic effect of E on mammary epithelial cell proliferation, the 3-fold increased proliferative response in mammary stromal cells is also noteworthy. Interestingly, proliferation of stromal cells occurred mainly in cells that were close to the proliferating epithelium of duct ends. We have previously shown that the local stromal environment has the capacity to influence mammary epithelial cell behavior and in particular can enhance epithelial cell response to E, possibly through the production of growth factors (Haslam, S. Z., et al., Endocrinol 129:2017–2023 (1991)). Furthermore, in vitro, under co-culture conditions, mammary epithelial cells have been shown to promote E-dependent stromal cell proliferation (Haslam, S. Z., Cancer Res 46:310–316 (1986)). Thus, the enhanced sensitivity of mouse mammary gland to E after long-term ovariectomy is likely to be mediated through estrogenic effects in the stroma. Furthermore, our results demonstrate that epithelial-stromal cell interactions may be bidirectional and epithelial cells may influence the proliferative response of nearby stromal cells.

A dissociation between E stimulation of cell proliferation and PR regulation in mouse mammary gland has previously been reported (Fendrick, J. L., et al., J Mammary Gland Biol Neoplasia 3:7–22 (1998)). Although E appears to mediate proliferation of epithelial cells indirectly via stroma, E acts directly in epithelial cells to increase PR levels (Haslam, S. Z., Endocrinol 122:860–867 (1988)). Thus, our observations of increased responsiveness to the proliferative effect, but decreased responsiveness to the PR regulatory effect of E indicate that mammary epithelial and stromal cells are affected differently by long-term OVX. To confirm this observation, we have also used immunohistochemical analysis to determine the percentage of PR positive cells and PR concentration per cell, using a fluorescein-conjugated secondary antibody detection system, similar to the ER immunofluorescence assay herein. In concordance with the ligand binding assay results we found that PR concentration per cell increased 2-fold in the 1 wk post OVX E-treated mammary glands, but there was no significant increase in either the numbers of PR positive cells or amount of PR per cell in the 5 wk post OVX E-treated glands. Future studies are planned to determine the mechanistic basis of these different responses to OVX. A similar dissociation of estrogenic regulation of proliferation and PR level has recently been reported for normal human breast (Clark, R. B., et al., Cancer Res 57:4987–4991 (1997)). It has been proposed that E acts indirectly to stimulate proliferation of normal human breast epithelium since ER and markers of cell proliferation do not co-localize in the same epithelial cells. In contrast, since ER and PR do co-localize in the same cells, E appears to act directly to regulate PR in breast epithelial cells. These additional similarities between the human and mouse mammary gland increase the attractiveness of the mouse model to study hormonal responsiveness of the postmenopausal breast.

Heightened sensitivity to the mitogenic effects of estrogen after withdrawal from estrogen has been previously reported to occur in the MCF-7 human breast carcinoma cell line (Masamura, S., et al., J Clin Endocrinol Metab 80:2918–2925 (1995)). A shift in the dose for maximal proliferative response to estradiol from $10^{-10}$M to $10^{-14}$ M was observed in cell culture when MCF-7 cells were deprived of estrogen for 1–6 months. While there was a 4-fold increase in ER concentration, the authors concluded that this alone could not account for increased sensitivity to E; no differences in receptor ligand binding affinity were observed in these studies. The enhanced sensitivity to the mitogenic effect of E was also observed in vivo. Nude mice implanted with the E-deprived cells demonstrated an earlier appearance of palpable tumors in response to E than animals bearing wild-type cells. While no specific mechanism(s) has been identified to explain the increased E-sensitivity in E-deprived MCF-7 cells, it does not appear to be the same as the enhanced proliferative response obtained herein after long-term OVX. In the case of the MCF-7 cells a shift in the dose response curve was observed that rendered the E-deprived cells maximally responsive to lower doses of E. In contrast, in the present study, maximal proliferative response was obtained at the same E dose in long-term and short-term OVX mice. However, the extent of the response was higher in the duct ends of long-term OVX mice. Furthermore, no significant difference in ER content between the two groups was observed herein. We have also examined proliferative response to E in our model after implanting small doses of E into the mammary gland in order to assess the direct effect of E on the mammary gland vs. E-induced systemic factors, such as hormones or growth factors/growth inhibitors produced elsewhere in the body (Muldoon, T. G., Endocrinol 109:1339–1346 (1981); Keough, E. M., et al., Tissue Cell 11:773–780 (1979); Das, R., et al., J Mammary Gland Biol Neoplasia 2:29–39 (1997); Sirbasku, D. A., Proc Natl Acad Sci 75:3786–3790 (1978); and Soto, A. M., et al., Endocrinol Rev 8:44–52 (1987)). Interestingly, the results obtained with systemically administered E herein, were virtually identical to those obtained with E implants with regard to the enhanced proliferation, the histological and morphological characteristics of the response and lack of PR inducibility. This suggests that the major effect of estrogen on mammary cells is direct and not due to systemically induced factors.

To our knowledge, only one other in vivo model, the cynomolgus macaque, has been developed to study the effect of HRT on the postmenopausal mammary gland (Cline, J. M., et al., Am J Obstet Gynecol 174:93–100 (1996)). In the cynomolgus macaque, a postmenopausal state was surgically induced by long-term ovariectomy (2 yrs). Long-term treatment of postmenopausal monkeys with estrogens for 36 months resulted in increased thickness and percentage of epithelial tissue and increased epithelial cell proliferation (Cline, J. M., et al., Am J Obstet Gynecol 174:93–100 (1996)). Thus, the results obtained after E treatment in the monkey after long-term OVX agree with our findings of increased E-induced epithelial cell proliferation after long-term OVX in the mouse.

In women, with the cessation of ovarian function after menopause, there is a significant reduction in the mitotic activity of mammary tissue (Walker, K. J., et al., Br J Cancer 64:764–768 (1991)). In a recent report, very low levels of mammary epithelial cell proliferation were reported in breast biopsies obtained from postmenopausal women receiving estrogen HRT (Hargreaves, D. F., et al., Br J Cancer In Press (1998)). Although not specified, it is likely that these samples were obtained from women who initiated estrogen HRT in the early postmenopausal period, since that is the time when the majority of women start HRT. In this regard, the low level of E-induced mammary cell proliferation in short-term OVX mice is compatible with the finding of low estrogen-induced breast cell proliferation in women when HRT is initiated in the early postmenopausal period. In the same study, the women receiving estrogen HRT also had elevated PR levels in their breast tissue. Thus, another similarity between the short-term OVX, early postmenopausal mouse and early postmenopausal human breast is increased PR after estrogen treatment.

The increased incidence of breast cancer in postmenopausal women may be simply coincidental with advanced age. Alternatively or in addition, it is possible that there is something specific about the postmenopausal breast that enhances the development of mammary cancer. A significant percentage of postmenopausal breast cancers are hormone responsive and regress in response to antiestrogen therapy (Lippman, M. E., et al., Cancer 46:2829–2834 (1980)). It seems paradoxical that breast cancers which are quite ovarian hormone responsive, arise at a time when ovarian function has ceased and the influence of these hormones appears to be minimal. One interpretation is that breast cancers may arise from and/or be comprised of cells which are supersensitive to the growth promoting effects of estrogen. Our present studies in mice suggest that altered hormonal milieu and long-term deprivation of ovarian hormones, rather than advanced age may be the major contributing factor to enhanced sensitivity to E observed in mice and raises the question of whether enhanced sensitivity to estrogen occurs after menopause in the human breast. The current results obtained in mice, considered in conjunction with results of estrogen HRT obtained in the monkey model and in postmenopausal women lead us to propose that the timing of initiation of HRT with estrogen in early postmenopausal vs. late postmenopausal women could have different consequences for the proliferative response of mammary cells to estrogen. These results have added significance because of a potential new pattern of timing of HRT in women. Previously, women started HRT in the early postmenopausal period to alleviate menopausal symptoms. However, with reports that HRT has beneficial effects on bone density and cardiovascular health in older women, late postmenopausal women who never received HRT in early postmenopause are now being prescribed HRT (Michaelsson, K., et al., Br Med J 316:1858–1863 (1997); Prelevic, G. M., et al., Bailliere's Clinical Endocrinology and Metabolism 11:311–340 (1997); Leveille, S. G., et al., J Am Geriatr Soc 45:1496–1500 (1997); and Miller, K. L., Clin Obst Gynec 39:912–932 (1996)). Our findings of enhanced proliferative response to E with increasing length of time after ovariectomy suggest the possibility that the proliferative response of older, late postmenopausal women receiving HRT for the first time may be greater than that of early postmenopausal women. Furthermore, if increased breast cancer risk associated with estrogen HRT in women is due to the mitogenic effect of estrogen in breast tissue, then the timing of HRT could also play a crucial role.

Clearly, hormonal responsiveness of the postmenopausal human breast needs to be investigated more thoroughly in order to better understand and assess the potential consequences of HRT. An important approach to this problem is the development of suitable experimental animal model systems. We propose that induction of short vs. long-term ovariectomy in mice is one such model system and may provide important information about potential alterations in hormonal responsiveness of the early and late postmenopausal human breast.

To advance understanding of the effects of HRT on the early vs. late postmenopausal breast an oviariectomy (OXX)-induced murine postmenopausal model was developed. OVX-induced menopause has been used in the cynmolgus macque for the study of HRT effects on breast tissue. HRT effects the normal human breast showed no differenes in proliferation. Indices associated with E alone HRT between women who had undergone surgical, OVX-induced menopause vs natural menopause supporting the validity of using surgery to induce menopause in an animal model (Hofseth, D. J. et al., J Clin Endocrinol Metab 84:4559–4565 [1999]).

In OVX mice, serum estradiol baseline level is reached by 24–48 h post OVX and the shortest period of time required for the mammary gland to achieve a baseline against which responses to exogenously administered hormones can be measured is 1 week (wk) post OVX (Haslam, S. Z., Endocrinology 122:464–470 (1998); Haslam, S. Z. et al., Endocrinology 108:825–830 (1981); Haslam, S. Z., et al., J Steroid Biochem Mol Biol 42: 589–595 (1992); Ankrapp, D. P., et al., J Cell Physiol 174:251–260 (1998)). Thus, 1 wk post OVX was chosen to represent an early postmenopausal state in the murine model. To simulate a late postmenopausal state, we have investigated the mammary gland response to exogenous estrogen at various times after OVX (Raafat, A. M., et al., Endocrinology 140:2570–2580 (1999)). Beginning at 5 weeks and up to 20 weeks post OVX, HRT with E alone produced 6.5-and 4-fold greater mitogenic responses in mammary epithelial and stromal cells respectively, than in at 1 wk post OVX. Between 5 and 20 wks post OVX the enhanced proliferative response to E was maintained. Thus 5 wk post OVX was chosen to simulate a late postmenopausal state in the mouse.

In humans natural menopause occurs with advanced age, with a mean age at menopause of 50 years. Therefore we investigated the age component was investigated in reproducing a postmenopausal status in mice. It was found that the mammary gland response to E in OVX young adult mice (10 wks of age) and OVX "middle-aged" mice (9–12 months old) was identical and was dependent on the length of time post OVX and not on age. These results suggest that altered hormonal milieu and long-term deprivation of ovarian hormones, rather than advanced age are the major contributing factors to the observed differences in response to E alone HRT in the murine model. The purpose of the present study was to examine the proliferative effects of long-term combined treatment with E+P on the mammary gland in a murine model of early and late postmenopause.

EXAMPLE 2

The aim was to analyze the proliferative response of the normal mammary gland to combined hormone replacement therapy (HRT) with estrogen (E) and progesterone (P) in a murine model of early vs. late postmenopausal states.

Ovariectomized (OVX) mice were injected daily for up to 56 days with E+P starting at either 1 or 5 weeks post OVX to simulate early and late postmenopause, respectively (Raafat, A. M., et al., Endocrinology 140:2570–2580 (1999)). At various times after treatment, proliferation was analyzed by DNA histoautoradiography and wholemount analyses. Progesterone receptor (PR) induction by E was also analyzed. To distinguish between E and P specific responses, the effects of the antiprogestin, RU486 or the antiestrogen, ICI 182,780 were tested.

The acute response to E+P in early postmenopause resulted in duct end enlargement, ductal sidebranching, and alveolar bud formation with 57-fold and 100-fold increased in proliferation duct ends and sidebranches, respectively. This was due the dominant effect of P acting through PR. In late postmenopause, the acute response produced only duct end enlargement; the 64-fold increase in epithelial cell proliferation was due to the dominant effect of E. After long-term treatment both early and late postmenopausal glands exhibited similar morphologies and 11 to 17-fold higher steady state epithelial proliferation than control-treated groups.

Starting combined E+P HRT in either early or late postmenopause produced a persistent, steady state 11 to 17-fold increase in epithelial cell proliferation which could be a contributing factor to increased breast cancer risk. The acute response in late postmenopause mimics the hormonal response of the pubertal mammary gland, which in rodents is the stage most susceptible to carcinogen-induced mammary tumorigenesis. These observations raise questions about increased susceptibility of the late postmenopausal gland to carcinogenesis and a role of HRT in the promotion of tumorigenesis.

Materials and Methods

Chemicals

[17B-methyl-3H]promogestone (R5020; S.A. 71 Ci/mmol) and radioinert R5020, and unlabeled 17β-estradiol (E) were purchased from New England nuclear Corp. (Boston, Mass.). RU 486 was a gift from Roussel Uclaf (Romainville, France). The antiestrogen, ICI 182,780 was a gift from ICI Pharmaceuticals (Macclesfield, Cheshire, England). [Methyl-3H]thymidine (S.A. 50 Ci/mmol) was purchased from ICN Radiochemical Corp. (Irvine, Calif.). All other chemicals and hormones were purchased from Sigma Chemical Co. (St. Louis, Mo.). Ethylene/vinyl copolymer (Elvax 40P, 40% vinyl acetate by weight) was a gift from Dupont (Wilmington, Del.).

Animals

Ten-week old BALB/c virgin mice from our own colony were bilaterally ovariectomized 1 or 5 weeks (wks) before hormone treatment. All mice received sc daily injections of 1 μg 17b-estradiol (E)+1 mg progesterone (P) as a suspension in 0.04% gum arabic in 0.85% NaCl; control groups received vehicle only. The E+P dosage was determined from previous studies on mouse mammary gland (Magnusson, C., et al., Int J Cancer 81:339–344 (1999); and Beral V., et al., Lancet 350:1047–1059 (1997)) on the basis that it produced modest sidebranching and alveolar bud development (FIG. 1) (Haslam, S. Z., Endocrinology 122:464–470 (1998)), and resembled the normal breast tissue of postmenopausal women who had received E+P HRT (Hofseth, L. J., et al., J Clin Endocrinol Metab 84:4559–4565 (1999)). In the implant studies, Elvax pellets containing either 0.1 mg RU486, 0.1 mg ICI 182,780 (doses that affected the implanted glands only, ruling out systemically mediated effects) or 0.85% NaCl (vehicle control) were prepared and implanted as previously described (Haslam, S. Z., Endocrinology 122:860–867 (1988)). The effects of the implants on the mammary gland were quantified morphometrically by capturing a digitized microscopic image of the mammary gland wholemount at 10x magnification using NIH/Image One software. The numbers and size of duct ends were measured within a 2 cm radius of the implant. Duct ends were considered to be enlarged if they were 1.0 mm or greater in diameter at the 10x magnification.

DNA Histoautoradiography

On days 3, 7, 14, 21, 42 and 56, after a single ip injection of $^3$H-thymidine (2 mCi/g body weight) 1 hr before sacrifice, mammary glands were processed for wholemount and autoradiographic analysis of epithelial and stromal cell labeling indices as previously described with the aid of a computer-interfaced morphometric digitizing system(Haslam, S. Z., Endocrinology 122:464–470 (1998)).

Steroid Hormone Binding Assay

Hormone- or control-treated mammary glands were analyzed for progesterone receptor (PR) levels using a dextran-coated charcoal ligand binding assay (Haslam, S. G., Endocrinology 195:789–795 (1979)). Tissue DNA was quantitated as previously described (Ceriotti, G., J Biol Chem 198:297–303 (1952)).

Immunohistochemistry

Frozen sections (7 μm) were fixed in 10% formalin in phosphate buffered saline, pH 7.3 (PBS) for 10 min followed by two 5 min PBS rinses. Sections were then incubated in 3% hydrogen peroxide in 100% methanol for 10 min followed by 2 PBS rinses. After a blocking step (1% bovine serum albumin in PBS for 20 min), sections were incubated for 2 hr with primary antibody (2 mg/m rabbit polyclonal PR antibody, Santa Cruz Biotechnology Inc., Santa Cruz, Calif.) or normal rabbit serum (negative control). Signal was amplified with biotinylated swine anti-rabbit IgG (1:200, Dako Corp. Carpenteria, Calif.) followed by horseradish peroxidase-conjugated avidin-biotin complex (Vector Laboratories Inc., Burlingame, Calif.) and diaminobenzidine tetrahydrochloride (Pierce Biotec Co., Rockford, Ill.). All steps were carried out at R.T. PR positive cells were identified by the presence of nuclear staining. The numbers of positive cells were quantified as described previously (Haslam, S. Z., et al., J steroid Biochem Mol Biol 42:589–595 (1992)).

Statistical Analysis

All data are expressed as the mean±SEM, and statistical significance was determined by analysis of variance or Student's t-test as appropriate.

Results

Effect of Combined E+P Treatment on Mammary Gland Morphology

The predominant effect of exogenous E+P in OVX adult mice is proliferation of the epithelium resulting in ductal sidebranching and alveolar bud formation. Wholemount analyses of early and late postmenopausal mammary glands showed that E+P treatment caused a combination of duct end enlargement and ductal sidebranching (FIG. 1). Treatment with E+P for 3 days caused only enlargement of duct ends in late postmenopausal (5 wk post OVX) mice and a combination of duct end enlargement and ductal sidebranching in early postmenopausal (1 wk post OVX) mice (FIGS. 1c,d). After 7 days of treatment ductal sidebranching was observed in both the 1 and 5 wk post OVX group, but to a greater extent in 1 wk post OVX mice; maximal sidebranching was observed after 14 days of treatment in both groups (FIGS. 1e,f). The amount of sidebranching decreased with continued treatment and reached a steady state level between 28–42 days of treatment (FIGS. 1g,h). No duct end stimulation or ductal sidebranching were observed in control-treated groups (FIGS. 1a,b).

Effect of E+P on Mammary Gland Cell Proliferation

Proliferation was quantified by histoautoradiography and labeling indices (LIs) were determined in specific epithelial structures i.e. ducts, duct ends, and sidebranches (FIG. 2). Proliferation in duct ends was highest after 3 days of treatment and was increased 57- and 64-fold in 5 wk and 1 wk post OVX mice, respectively. Proliferation in sidebranches was maximal after 3 days of treatment in 1 wk post OVX group and was increased 100-fold over the control-treated group. In the 5 wk post OVX group, maximal proliferation in sidebranches occurred later, after 14 days of treatment and was 78-fold greater than in the control group. By day 21 the LIs in sidebranches had declined and were similar in both 1 and 5 wk post OVX mammary glands. However, these reduced, steady state levels of proliferation remained significantly, 15 to 17-fold higher than in control-treated groups.

Labeling indices were also determined for mammary stromal cells. Proliferation in 1 wk post OVX mice after 3 days of treatment with E+P was greatest in stromal cells adjacent to sidebranches (FIG. 3). In 5 wk post OVX mice, proliferation after 3 days of treatment was greatest in stromal cells adjacent to duct ends. Thereafter, the highest stromal cell LIs were found adjacent to epithelial sidebranches in both 1 and 5 wk post OVX mice. Thus stromal cell proliferation was consistently localized to cells in close proximity to proliferating mammary epithelium. These results suggest positive paracrine interactions between mammary epithelial cells and adjacent stromal cells.

Stimulation of Duct End Proliferation by E or P

Previously, in studies of the effect of HRT treatment with E alone in the mouse postmenopausal model, duct end stimulation had been observed only in E-treated 5 wk post OVX mice; no duct end stimulation was observed in E-treated 1 wk post OVX mice (Raafat, A. M., et al., Endocrinology 140:2570–2580 (1999)). In order to determine if duct end stimulation in 1 wk post OVX mice treated with E+P was due to the action of E or P the effect of the anti-progestin, RU 486 was tested. This was accomplished by using the Elvax 40P pellet implantation technique which allows delivery of bioactive molecules such as RU486 in a small dose that is confined to the implanted mammary gland. Wholemounts of RU486 and control implanted glands were examined after 3 days of E+P injection. As can be seen in FIG. 4e duct end enlargement and sidebranching were significantly inhibited by RU486 implants in the 1 wk post OVX group, but not in the 5 wk post OVX group (FIG. 4f). Quantitation of the effects of RU486 showed that RU486 implants significantly reduced the number of enlarged duct ends induced Dy E+P injection by 9-fold in 1 wk post OVX but not in the 5 wk post CVX group (Table I). Implantation of 5 wk post OVX glands with the anti-estrogen, ICI 182,780, inhibited duct end enlargements induced by E+P (FIG. 5) and the numbers of enlarged duct ends were reduced 8-fold (Table II). These results demonstrate that duct end stimulation in the late postmenopausal gland was not due to the action of P but due to E.

TABLE I

Effect of RU486 implants on duct end enlargement in early and late postmenopausal mammary glands of mice injected with E + P.

| | Implant Treatment | |
|---|---|---|
| Postmenopausal Status | Control | RU486 |
| Early postmenopause (1 wk post OVX) | $6.5 \pm 0.75^a$ | $0.75 \pm 0.25*$ |
| Late postmenopause (5 wk post OVX) | $7.0 \pm 1.5$ | $9.0 \pm 1.0$ |

$^a$The number of enlarged duct ends (mean ± S.E.M.) per implanted mammary gland determined morphometically as described in Materials and Methods. One and 5 wk post OVX mice were implanted with 0.1 μg RU486 into the right inguinal gland and the contralateral left inguinal gland received a control implant. Mice were then injected for 3 days with E + P before wholemount analysis. Each group contained 5–8 mice.
*p = 0.01 that the number of enlarged duct ends in the RU 486-implanted glands of 1 wk post OVX mice were less than the contralteral, control-implanted glands and both control- and RU489- implanted glands of 5 wk post OVX mice.

TABLE II

The effect of ICI 182,780 implants on duct end enlargement in late postmenopausal mammary glands of mice injected with E + P.

| | Implant Treatment | |
|---|---|---|
| Postmenopausal Status | Control | ICI 182.780 |
| Late postmenopause 5 wk post OVX | $8.0 \pm 1.5^a$ | $1.0 \pm 1.0*$ |

$^a$The number of enlarged duct ends (mean ± S.E.M.) per implanted mammary gland was determined morphometically as described in Materials and Methods. Five wk post OVX mice were implanted with 0.1 μg ICI 182, 780 into the right inguinal gland and the contralateral left inguinal gland received a control implant. Mice were then injected for 3 days with E + P before wholemount analysis (n = 8 mice).
*p = 0.01 that the number of enlarged duct ends in the ICI 182.780-implanted glands of 5 wk post OVX mice were less than the contralateral, control-implanted glands.

Figures 6A, 6B:
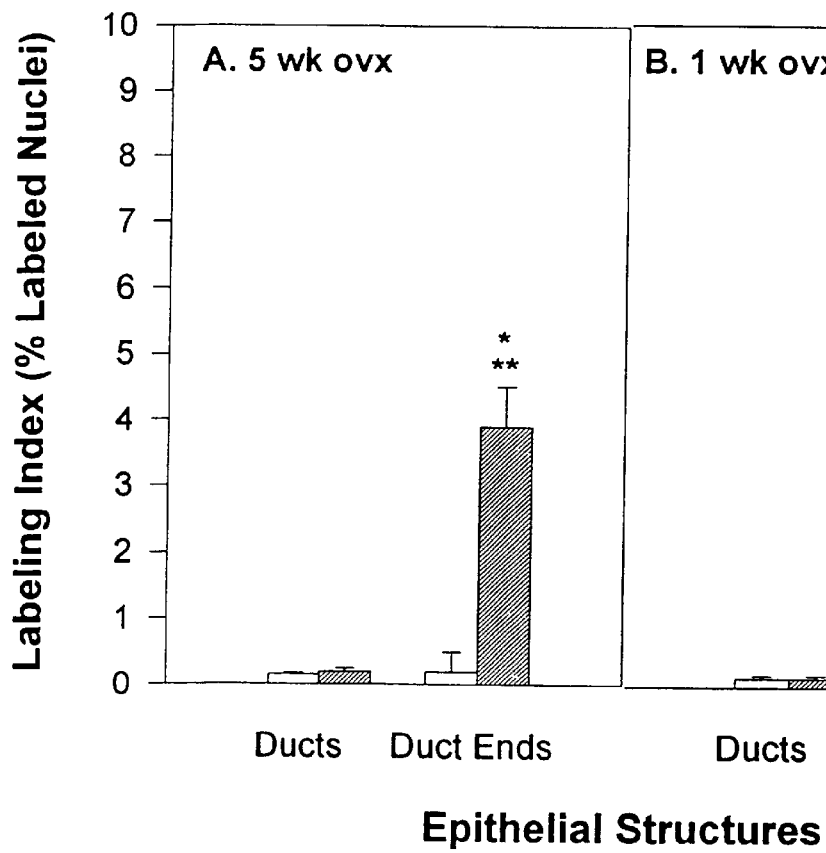
FIGS. 6A and 6B are graphs showing E-induced proliferation in ducts vs duct ends at 1 or 5 wk post OVX. Mice were OVX (6A) or (6B) 5 wk prior to a single ip injection with 1 μg E or 0.85% NaCl (C). After 72 h, $^3$H-thymidine was injected ip and mammary glands were removed 1 h later and processed for DNA histoautoradiography as described in Materials and Methods. LIs were determined separately for ducts vs duct ends. Each bar represents the M±SEM of a minimum of 50 individual structures and a minimum of 2500 cells for each experimental group; n=5 and 9 mice per group at 1 and 5 wk post OVX, respectively. * p=0.02–0.001 that LI of duct ends in E-injected glands was significantly greater than LIs of all ducts or duct ends in control-treated glands. ** p=0.001 that LI of duct ends in E-treated mice at 5 wk post OVX was significantly greater than that in E-treated mice at 1 wk post OVX.

E-induced increase in PR levels in mammary epithelium has been previously shown to be closely correlated with the P-dependent proliferation that results in ductal sidebranching and is the basis for the synergistic proliferative response to E+P treatment. Since proliferation in ductal sidebranches in 5 wk post OVX mice was delayed compared with 1 wk post OVX mice (FIG. 2), we analyzed the effects of E on PR levels in the two groups. FIG. 6 shows that a single injection of E failed to increase PR levels in 5 wk post OVX gland, whereas there was a 2.5-fold increase in PR levels observed in 1 wk post OVX mice. PR levels in 5 wk post OVX mice were not increased above control levels until the mice had received 7 daily E injections. Immunohistochemical analysis showed that there were ~2-fold more PR positive cells in duct ends and ducts of 1 wk post OVX mice compared to 5 wk post OVX mice (Table III). Thus, the delayed E-dependent increase in PR was most likely responsible for the delayed development of ductal sidebranching and of proliferation in ductal sidebranches in the late postmenopausal mammary gland.

TABLE III

Immunohistochemical analysis or PR positive cells in mammary gland of early and late postmenopausal mice injected with E + P.

| | Hormone Treatment | |
|---|---|---|
| Postmenopausal Status | Control | E + P |
| Early postmenopause (1 wk post OVX) | $3.5 \pm 0.75^a$ | $10.5 \pm 1.25*$ |
| Late postmenopause (5 wk post OVX) | $3.0 \pm 1.5$ | $3.5 \pm 1.0$ |

$^a$One or 5 wk post OVX mice were injected for 3 days with E + P or vehicle control and the percent of PR positive epithelial cells (mean ± S.E.M was determined immunohistochemically as described in Materials and Methods. Each experimental group contained 5 mice and a minimum of 1000 cells were counted in each group
*p = 0.05 that the percent of PR positive cells in E + P injected 1 wk post OVX mice was greater than in all other groups.

Comments

Because of the beneficial effects of HRT older women who had not previously taken HRT are now receiving HRT in late postmenopause. The consequences of early vs. late timing of HRT on breast tissue proliferation and possible influence on breast cancer risk are unknown. Previously, we found that timing of HRT with E alone had very different effects in the early vs. late postmenopausal mouse mammary gland (Raafat, A. M., et al., Endocrinology 140:2570–2580 (1999)). In the present report we have examined both the acute and long-term effects of combined treatment with E+P in a murine model of early and late postmenopause. We found notable differences between the two groups in their early phase, acute responses to E+P. However, after long term, daily E+P treatment, under steady state conditions both early and late postmenopausal groups exhibited similarly increased epithelial cell proliferation and ductal sidebranching. Both the steady-state proliferative responses were elevated 11 to 17-fold compared to untreated, control mice. These results suggest, that early vs. late postmenopausal timing of combined E+P HRT in women may result in similar long-term proliferative effects on breast tissue. Thus, the overall result of persistent increased epithelial cell proliferation in both early and late postmenopausal states as a result of combined E+P HRT could be a significant contributing factor to increased breast cancer risk observed in women receiving E+P HRT (Beral, V., et al., Lancet 350:1047–1059 (1997)).

The results demonstrating elevated proliferation indices as a result of E+P HRT obtained in the present study in mice are in good agreement with the monkey postmenopause model as well as with the recent results demonstrating elevated epithelial proliferation indices obtained with normal human breast tissues from postmenopausal women receiving E+P HRT (Hofseth, L. J., et al., J Clin Endocriol Metab 84:4559–4565 (1999)). Thus, the similarity among these findings on the effects of HRT in the mouse, monkey and human support the relevance of the murine postmenopausal model.

Interestingly, the early, acute response to E+P treatment was a stimulation of the duct ends in both early and late postmenopausal mice. This was surprising because we had previously shown that duct end enlargement was observed as a response to E treatment only in the late postmenopausal mammary gland (Raafat, A. M., et al., Endocrinology 140:2570–2580 (1999)). In the present study, we determined that the enlarged duct ends in the early postmenopausal mammary glands treated with E+P were the result of P action since implants of the anti-progestin RU 486 into the mammary gland blocked this response. In contrast to its effect in the early postmenopausal mice, RU486 failed to block duct end enlargement in the late postmenopausal mice. The ability of the antiestrogen, ICI 182,780 to block duct end stimulation, confirms that E and not P mediated this morphological response in the late postmenopausal mammary gland.

Ductal sidebranching is dependent on the presence of epithelial PR (Haslam, S. Z., Endocrinology 125:2766–2772 (1989); Humphreys, R. D., et al., Mol Endocrinology 11:801–811 (1997); and Fendrick, J. L., et al., J Mammary Gland Biol Neoplasia 3:7–22 (1998)). We had previously shown that in the late postmenopausal mammary gland PR levels are low and not rapidly inducible by E (Raafat, A. M., et al., Endocrinology 140:2570–2580 (1999)). In the present study there was a delay in the ductal sidebranching response to E+P treatment in late postmenopausal mice. Thus, it seemed likely that the basis for this differential sidebranching response was the result of differences in mammary PR concentration and E-inducibility of PR between the two groups. This was confirmed by an analysis of time course of PR induction by E in early vs. late postmenopausal mice. PR levels were increased 2-fold after a single injection of E in early postmenopausal mice. However, 7 daily E injections were required to increase PR levels in the late postmenopausal gland. Thus, the rapid induction of PR in the early postmenopausal mammary gland (day 1) correlates well with early development of ductal sidebranching (day 3). Conversely, the delayed induction of PR in late postmenopausal mammary gland (day 4–7) is correlated with delayed development of sidebranching (day 7). The reduced amount of PR in late postmenopausal mice was also confirmed by immunohistochemical analysis of PR positive cells.

We have previously reported that the late postmenopausal mammary gland response to short-term treatment with E alone, characterized by the enlargement of duct ends and lack of PR inducibility, is remarkably similar to the response of the immature, pubertal gland. In the present report, the requirement of multiple treatments with E+P or E (4–7 days) in order to obtain ductal sidebranching and PR inducibility respectively, in the late postmenopausal gland is also similar to the immature gland (Haslam, S. Z., et al., Steroid Biochem 12:27–34 (1993)). This provides further evidence of shared characteristics of hormonal responsiveness between the pubertal, immature and adult, late postmenopausal mammary glands. Since the prepubertal and late postmenopausal states are both characterized by low levels of ovarian hormones, it is tempting to speculate that the acute proliferative and morphological responses of the mammary gland to E and lack of response to P at puberty and late postmenopause are related to the effects of hormone deprivation. The mechanisms involved are currently unknown, but are not a consequence of altered estrogen receptor levels or binding affinity (Raafat; A. M., et al., Endocrinology 140:2570–2580 (1999)).

In rodent models of mammary carcinogenesis, the immature, pubertal stage of mammary gland development is the most susceptible to tumor development (Russo, I. H., et al., J Mammary Gland Biology and Neoplasia 3:49–61 (1998)). In this regard, our observation that there are striking similarities between the late postmenopausal and pubertal mammary glands in the murine animal model raises questions about susceptibility of the late postmenopausal gland to carcinogenesis and the role of HRT in the promotion of mammary tumorigenesis. Experimental studies of mammary carcinogenesis in the postmenopausal murine model system are currently in progress and could provide answers to these questions.

The highest incidence of breast cancer occurs in postmenopausal women. This raises the possibility that the hormonal responsiveness of the postmenopausal breast enhances the development and/or expression of breast cancer. In the human breast, the postmenopausal state is characterized by regression of the breast epithelium (Haslam, S. Z., et al., Steroid Biochem 12:27–34 (1993)). Morphological analysis of the human breast has revealed that the predominant epithelial structure present in breasts of adolescent females (ages 14–18) and young adult females (ages 19–23) is the undifferentiated type I lobule (Russo, J., et al., Breast Canc Res Treat 23:211–218 (1992); and Russo, J., et al., Role of hormones in human breast development: the menopausal breast. In: "Progress in the Management of Menopause" Parthenon Publ., London 184–193 (1997)). Thereafter there is a decrease in the type I lobule and an concomitant shift to the more differentiated type II and III lobules as a function of advancing age and pregnancy. After menopause there is shift back to a preponderance of type I lobules. Russo and colleagues suggest that the type I lobule is similar to terminal end buds of immature rodents. In rodents the terminal end bud is the site of origin of carcinogen-induced mammary carcinomas (Russo, J., et al., Breast Cancer Res Treat 39:7–20 (1996)). If the morphological similarly of postmenopausal human breast to the adolescent breast is also accompanied by increased sensitivity to the hormones in HRT as it is in the mouse, subsequent exposure to both carcinogens and HRT could conceivably have implications for increased breast cancer risk. Further studies in postmenopausal animal models may provide a better understanding of the nature of hormonal responsiveness of the postmenopausal breast and the potential consequences of HRT and breast cancer risk.

This invention provides an animal model of aging in women that includes specific postmenopausal status (early vs. late) and reproductive history (nulliparous vs. parous). This animal model is to be used for the rapid screening of the effects on all organ systems on gene regulation and biological function of biological effector molecules such as, but not limited to, hormones, cytokines, growth factors), drugs (such as, but not limited to, hormone replacement therapy drugs, drugs to treat chronic and acute diseases and cancers), drug interactions, testing of chemopreventive agents, testing of pharmacology and biological response to xenobiotics, environmental bioreactive substances, suspected and known toxins and carcinogens. In this model menopause is surgically-induced by bilateral ovariectomy carried out in mature adult or aged nulliparous or parous mice and early and late postmenopausal states are represented by 1 or 5–20 weeks post-ovariectomy.

(1) Relevance of the Model

Previous models of aging in females in animal models have not included menopausal status. Effects of hormones, drugs, xenobiotics etc. may have profoundly different effects in many if not all organ systems as a consequence of menopause. In particular, there may be important differences in biological responses in all organ system depending in early vs. late postmenopausal status and reproductive history. For example, in previous approaches to the study of the effects of hormone replacement therapy (i.e. in the monkey) the concept of early vs. late postmenopausal status was not considered. In women postmenopausal hormone replacement therapy often begins in the early postmenopausal period (45–55 years of age). However, because of the proposed benefits of HRT on cardiovascular disease, osteoporosis and on cognitive function and Alzheimer's disease, older women in their seventies, who had never taken HRT in early postmenopause are now being prescribed HRT in late postmenopause. This mouse model has been developed to consider both early and late postmenopausal states. HRT has an effect on the normal human postmenopausal breast and it has been established that the proliferative effects of HRT with estrogen and estrogen+progestin in the human are very similar to that observed in the mouse model. An in vivo model is highly relevant because it takes into account the metabolic effects on drugs and hormones and ultimate delivery and effect on target tissues. These effects cannot be mimicked or determined in in vitro, cell culture systems. Thus drug testing must ultimately be carried out in animals. Therefore appropriate animal models are critical to drug development. The present animal model is based upon surgically-induced menopause by ovariectomy. Human studies have revealed that women who experienced surgically-induced menopause displayed the same response to HRT as did women who underwent natural menopause. Thus surgically-induced menopause is a relevant model for naturally occurring menopause.

(2) Rapidity of Results

Epidemiological studies of biological effector molecules (such as but not limited to hormones, cytokines, growth factors), drugs (such as but not limited to hormone replacement therapy drugs, drugs to treat chronic and acute diseases and cancers), drug interactions, testing of chemopreventive agents, testing of pharmacology and biological response to xenobiotics, environmental bioreactive substances, suspected and known toxins and carcinogens in humans can take many years to complete and may only provide associative rather than causal relationships due to the heterogeneous nature and numerous confounding variables present in human populations. The animal model provides rapid information, that is determined under experimentally controlled conditions, and allows the control and manipulation of relevant variables.

(3) Cost Effectiveness

The only other animal postmenopausal model that has been used is the monkey. This model system is extremely expensive and use of monkeys for research has been highly opposed by animal rights activists. In Europe, monkeys cannot be used for research at all. Furthermore, because of the longer life-span of the monkey, these studies take longer than studies in mice, further adding to cost.

(4) Markets for the Invention

Drug companies developing drugs that can benefit disease states in any organ system in aging women. Testing (FDA) of natural products (herbs and food stuffs, etc.) or chemicals that are to be used by aging, postmenopausal women. This animal model is to be used for the rapid screening of the effects on all organ systems of biological effector molecules (such as but not limited to hormones, cytokines, growth factors), drugs (such as but not limited to hormone replacement therapy drugs, drugs to treat chronic and acute diseases and cancers), drug interactions, testing of chemopreventive agents, testing of pharmacology and biological response to xenobiotics, environmental bioreactive substances, suspected and known toxins and carcinogens.

C & D. This model can be used for determination of response of the mammary gland, brain and uterus to hormone replacement therapy drugs. Organ systems such as but not limited to bone and cardiovascular system can be incorporated with the testing.

As used herein the term "biologically active agent" means chemical, mechanical and electrical and wave radiation agents which can affect the animal. Wave radiation includes light, x-ray, UV and IR radiation.

It is intended that the foregoing description be only illustrative of the present invention and that the present invention be limited only by the hereinafter appended claims.

I claim:

1. A method for determining a response to a biologically active agent in ovariectomized mice which comprises:
    (a) surgically ovariectomizing the mice at a baseline time to establish menopause in the mice;
    (b) monitoring the ovariectomized mice for serum estrogen after being ovariectomized and establishing a constant level of estrogen for the overiectomized mice;
    (c) dividing the ovariectomized mice of step (b) into at least two groups;
    (d) treating a first of the groups of the ovariectomized mice over time with the biologically active agent wherein the treating is initiated within a first period of time which is less than 21 days from the baseline time and which corresponds to early menopause in a human;
    (e) treating a second of the groups of the ovariectomized mice over time with the biologically active agent wherein the treating is initiated within a second period of time which is greater than about 35 days from the baseline time and which corresponds to late menopause in a human; and
    (f) comparing the results for the first and second groups of ovariectomized mice to determine the response to the biologically active agent.

2. The method of claim 1 wherein the biologically active agent is estrogen.

3. The method of claim 1 or 2 wherein the treatment with the biologically active agent begins about seven days for the first group and about 35 days for the second group.

4. The method of claim 2 wherein the mice are between about 10 weeks to one year old.

5. The method of claim 4 wherein the mice are about 10 weeks of age.

6. The method of claim 1 wherein the mice are in addition adrenalectomized.

7. The method of claim 1 wherein the biologically active agent is estrogen combined with a second biologically active agent.

8. The method of claim 7 wherein the second biologically active agent is progestin.

9. The method of claim 1 wherein mammary glands of the mice are biopsied to provide the comparison between the first and second groups of the mice.

10. The method of claim 9 wherein the mice are tested for tumorigenesis of the mammary glands.

11. A method for determining the effect of a biologically active agent on an organ system in ovariectomized mice that undergo hormone replacement therapy (HRT) after ovariectomy which comprises:
    (a) surgically ovariectomizing the mice at a baseline time to establish menopause in the mice;

(b) dividing the ovariectomized mice into at least two groups;

(c) administering the HRT over time to a first of the groups of the ovariectomized mice wherein the HRT is initiated within a first period of time which is within about 21 days from the baseline time and which is the period of time that corresponds to early menopause in the human;

(d) administering the HRT over time to a second of the groups of the ovariectomized mice wherein the HRT is initiated within a second period of time which is about 35 or more days from the baseline time and which is the period of time that corresponds to late menopause in the human;

(e) treating the ovariectomized mice in the first and the second groups being administered the HRT with the biologically active agent; and (f) determining the effect of the biologically active agent on the organ system of the mice being administered the HRT.

12. The method of claim 11 wherein the organ system is the mammary gland.

13. The method of claim 11 or 12 wherein the HRT comprises estrogen.

14. The method of claim 11 or 12 wherein the HRT comprises estrogen and progestin.

15. The method of claim 11 or 12 wherein the HRT is administered to the first group about seven days after the menopause has been established and the HRT is administered to the second group about 35 days after the menopause has been established.

16. The method of claim 11 wherein the mice are ovariectomized at about 10 weeks of age.

17. The method of claim 11 wherein the mice are ovariectomized between about 10 weeks of age and about one year of age.

18. The method of claim 11 or 12 wherein the mice are in addition are adrenalectomized.

19. The method of claim 11 or 12 wherein the HRT and the biologically active agent are administered to the mice simultaneously.

20. The method of claim 11 or 12 wherein the organ systems of the mice are biopsied to determine the effect of the biologically active agent on the organ systems of the mice.

21. The method of claim 11 or 12 wherein the effect that is determined is proliferation of particular cells of the organ system.

22. The method of claim 11 or 12 wherein the biologically active agent is not estrogen or progesterone.

23. A method for determining a response to a biologically active agent in mice that experience menopause when ovariectomized which comprises:

(a) surgically ovariectomizing the mice at a baseline time to establish menopause in the mice;

(b) monitoring the ovariectomized mice for serum estrogen after being ovariectomized and establishing a constant level of estrogen for the ovariectomized mice;

(c) dividing the ovariectomized mice of step (b) into at least two groups;

(d) treating a first of the groups of the ovariectomized mice over time with the biologically active agent wherein the treating is initiated within a first period of time after the baseline time which corresponds to early menopause in a human;

(e) treating a second of the groups of the ovariectomized mice over time with the biologically active agent wherein the treating is initiated within a second period of time after the baseline time which corresponds to late menopause in a human; and (f) comparing the results for the first and second groups of ovariectomized mice to determine the response to the biologically active agent.

* * * * *

UNITED STATES PATENT AND TRADEMARK OFFICE
CERTIFICATE OF CORRECTION

PATENT NO. : 6,583,334 B1
DATED : June 24, 2003
INVENTOR(S) : Sandra Z. Haslam

It is certified that error appears in the above-identified patent and that said Letters Patent is hereby corrected as shown below:

Column 4,
Line 12, "H-thymidine" should be -- $^3$H-thymidine --.
Line 55, " p 0.01" should be --  p = 0.01 --.
Line 60, "(6A) or (6B)" should be -- (6A) 1 or (6B) --.

Column 6,
Line 18, "from and 1 and" should be -- from 1 and --.

Column 7,
Line 11, "(16A, 16C, 1E)" should be -- (16A, 16C, 16E --.

Column 9,
Line 8, "histoautoradiogrpahy" should be -- histoautoradiography --.
Line 15, "histoautcradiographic" should be -- histoautoradiographic --.
Line 23, "400 pm" should be -- 400 $\mu$m --.

Column 13,
Line 3, "due an altered" should be -- due to an altered --.

Column 17,
Line 53, "(OXX)" should be -- (OVX) --.
Line 56, "effects the" should be -- effects on the --.
Line 56, "differenes" should be -- differences --.
Line 61, "Hofseth, D. J." should be -- Hofseth, L. J. --.

Column 21,
Line 12, "9-fold" should be -- 8-fold --.
Line 13, "CVX" should be -- OVX --.
Line 58, insert heading -- Effect of E treatment on PR levels --.

UNITED STATES PATENT AND TRADEMARK OFFICE
CERTIFICATE OF CORRECTION

PATENT NO.     : 6,583,334 B1
DATED          : June 24, 2003
INVENTOR(S)    : Sandra Z. Haslam It is certified that error appears in the above-identified patent and that said Letters Patent is hereby corrected as shown below:

Column 24,
Line 36, "similarly" should be -- similarity --.

Signed and Sealed this

Fourteenth Day of March, 2006

JON W. DUDAS
*Director of the United States Patent and Trademark Office*